(12) United States Patent
Shin et al.

(10) Patent No.: US 10,473,602 B2
(45) Date of Patent: *Nov. 12, 2019

(54) SELECTIVE SATURATION PULSE FOR DOWNHOLE MEASUREMENTS

(71) Applicants: Halliburton Energy Services, Inc., Housto, TX (US); Chang S. Shin, Albany, CA (US); Mark Cheiron Butler, Kingwood, TX (US)

(72) Inventors: Chang S. Shin, Albany, CA (US); Mark Cheiron Butler, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,419

(22) PCT Filed: Oct. 18, 2016

(86) PCT No.: PCT/US2016/057517
§ 371 (c)(1),
(2) Date: Apr. 13, 2018

(87) PCT Pub. No.: WO2017/112055
PCT Pub. Date: Jun. 29, 2017

(65) Prior Publication Data
US 2018/0321169 A1 Nov. 8, 2018

Related U.S. Application Data

(63) Continuation-in-part of application No. PCT/US2015/067266, filed on Dec. 22, 2015.

(51) Int. Cl.
*G01N 24/00* (2006.01)
*G01N 24/08* (2006.01)
(Continued)

(52) U.S. Cl.
CPC .......... *G01N 24/081* (2013.01); *E21B 47/12* (2013.01); *E21B 49/08* (2013.01); *G01R 33/448* (2013.01); *G01V 3/32* (2013.01); *G01R 33/583* (2013.01)

(58) Field of Classification Search
USPC ........................................ 324/303, 307–310
See application file for complete search history.

(56) References Cited

U.S. PATENT DOCUMENTS 5,212,448 A * 5/1993 Le Roux .............. G01R 33/446
324/307
5,253,271 A 10/1993 Montgomery
(Continued)

OTHER PUBLICATIONS

International Search Report and The Written Opinion of the International Search Authority, or the Declaration, dated Jan. 6, 2017, PCT/US2016/057517, 15 pages, ISA/KR.
(Continued)

*Primary Examiner* — Vincent Q Nguyen
(74) *Attorney, Agent, or Firm* — Haynes and Boone, LLP

(57) ABSTRACT

Various embodiments include a method for configuring and generating a non-adiabatic saturation pulse for use in nuclear magnetic resonance (NMR) logging. One such method configures the pulse by adjusting one or more of pulse amplitude modulation or phase cycling. The modified pulse is transmitted into a fluid such that a substantially uniform nuclear spin saturation or nuclear spin inversion echo response is received from the fluid. A wait time between the pulse transmission and the echo response that indicates that spin equilibrium has been achieved is substantially equal to a $T_1$ time. The wait time is an indication of the characteristics of the fluid.

17 Claims, 17 Drawing Sheets

(51) Int. Cl.
   *G01R 33/44*   (2006.01)
   *G01V 3/32*    (2006.01)
   *E21B 49/08*   (2006.01)
   *E21B 47/12*   (2012.01)
   *G01R 33/58*   (2006.01)

(56) References Cited

U.S. PATENT DOCUMENTS

| | | | |
|---|---|---|---|
| 6,064,207 | A | 5/2000 | Kupce |
| 6,094,049 | A | 7/2000 | Rosenfeld et al. |
| 8,324,898 | B2 | 12/2012 | Sung et al. |
| 2002/0167314 | A1 | 11/2002 | Prammer |
| 2003/0071617 | A1 | 4/2003 | Kruspe et al. |
| 2004/0257074 | A1 | 12/2004 | Appel et al. |
| 2005/0248342 | A1 | 11/2005 | Rottengatter et al. |
| 2007/0007959 | A1* | 1/2007 | Szyperski ......... G01R 33/4616 324/307 |
| 2010/0253340 | A1 | 10/2010 | Corum et al. |

OTHER PUBLICATIONS

International Search Report and The Written Opinion of the International Search Authority, or the Declaration, Sep. 21, 2016, PCT/US2015/067266, 13 pages, ISA/KR.

Tannús et al., "Adiabatic Pulses," NMR in Biomedicine, Dec. 1997, vol. 10, pp. 423-434.

* cited by examiner

SELECTIVE SATURATION PULSE FOR DOWNHOLE MEASUREMENTS

RELATED APPLICATIONS

The present application is a U.S. National Stage patent application of International Patent Application No. PCT/US2016/057517, filed on Oct. 18, 2016, which is a continuation-in-part of International Patent Application No. PCT/US2015/067266, filed on Dec. 22, 2015, which are incorporated herein by reference.

BACKGROUND

Nuclear magnetic resonance (NMR) logging is a type of well logging that uses the NMR response of a formation to determine its porosity and permeability, providing a continuous record along the length of a borehole. NMR logging exploits the magnetic moment of hydrogen, which is abundant in rocks in the form of fluids. The NMR signal amplitude is proportional to the quantity of hydrogen nuclei present in a formation and can be calibrated to give a value for porosity that is free from lithology effects.

NMR logs provide information about the quantities of fluids present, the properties of these fluids, and the sizes of the pores containing these fluids. From this information, it is possible to estimate the volume (porosity) and distribution (permeability) of the rock pore space, the rock composition, the type and quantity of fluid hydrocarbons, as well as the hydrocarbon producibility.

Generally, NMR tools operate by imposing a static magnetic field on a geological formation. This magnetic field is traditionally referred to as the "static field" as it is usually independent of time and is given the symbol $B_0$. A second magnetic field, which varies in time, is also applied. This field is typically designated as $B_1$ and is traditionally called the "radio frequency field". It is turned on and off at different increments, known as a pulse. This second, perturbing field is perpendicular to the static field, $B_0$. The perturbing field moves the magnetization away from the thermal equilibrium. Generating the perturbing field takes a significant amount of energy, which may be in short supply downhole, especially if the logging tool is powered by batteries.

A particular type of energy-consuming RF pulse is a broadband saturation pulse that may commonly be used for downhole NMR logging of the spin-lattice relaxation time ($T_1$) measurements. In a typical logging while drilling (LWD) NMR logging $T_1$ sequence, the single broadband saturation chirp pulse is energy inefficient and uses a cumbersome calibration process that is time consuming and affects operation efficiency.

DETAILED DESCRIPTION

Figure 1:
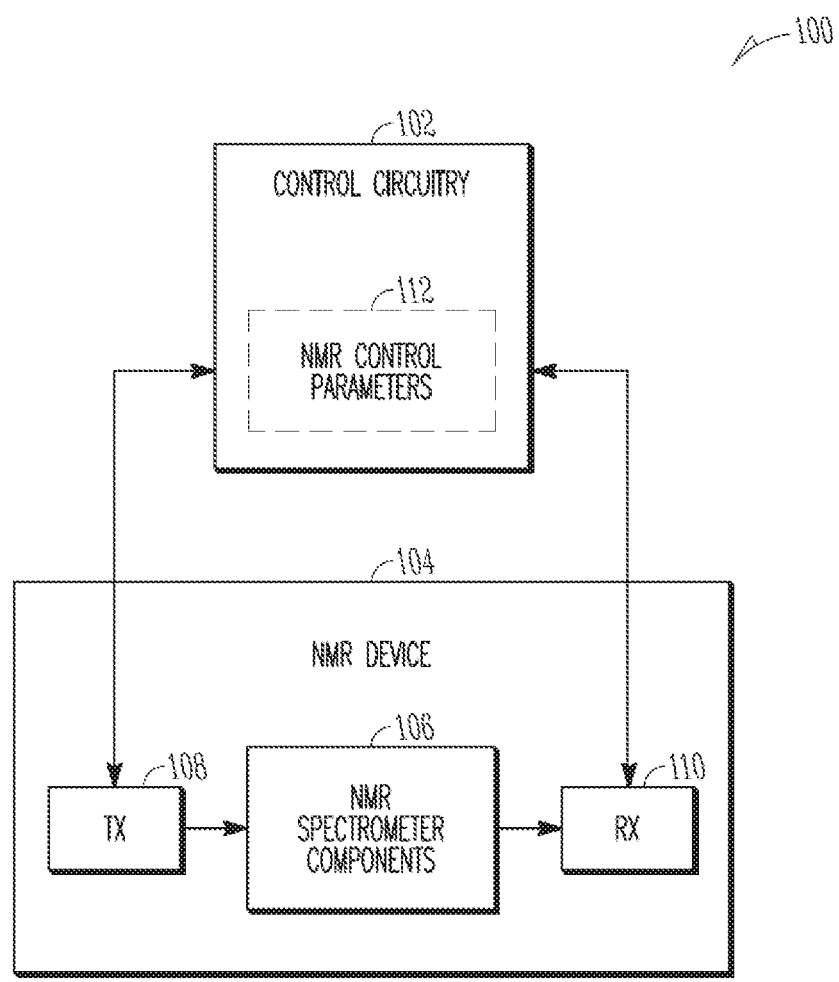
FIG. 1 is a diagram showing an NMR tool, according to various examples of the disclosure.

Some of the challenges noted above, as well as others, can be addressed by forming a saturation or inversion pulse that is generated in terms of bandwidth, selectivity, pulse length, total radio frequency (RF) energy consumption, and/or lower peak RF amplitude based on the logging application. By solving Bloch's equations for a $T_1$ measurement sequence and phase-cycling the $T_1$ measurement sequence, calibration procedures may be simplified and logging quality improved by suppressing undesirable signal contributions. Additionally, pulse parameters (e.g., pulse shape, bandwidth, selectivity, length, phase, frequency, total RF energy consumption, amplitude, phase cycling) may be selectively adjusted, as described subsequently, to increase NMR logging times without increasing energy usage. Solving the technical problem in this way can save energy, contributing to a more efficient NMR measurement process.

As used herein, adiabatic pulses may be defined as amplitude and frequency modulated RF-pulses where the orientation of the effective magnetic field changes much more slowly than the rotation of M about this effective field, so that M stays nearly aligned with the effective field during the pulse. Here M represents the spin magnetization that is the source of the NMR signal. The pulses utilize the adiabatic principle wherein the magnetization (M) is manipulated by a slow passage of the $B_1$ field through resonance. With adiabatic pulses, nuclear spins having different resonant frequencies are inverted or manipulated at different times. This differs from a rectangular or amplitude modulated (AM) RF-pulse where all nuclear spins are affected substantially simultaneously. An effective field may be defined as the magnetic field in a reference frame that rotates with the instantaneous frequency of the RF field.

Also as used herein, non-adiabatic pulses may be defined as RF-pulses that fail to satisfy the adiabatic condition, i.e., RF pulses where the orientation of the effective magnetic field changes too quickly for the magnetization M to follow it closely during the pulse.

A sinc pulse may be one example of a non-adiabatic pulse. A sinc pulse is generated using only amplitude modulation and not frequency modulation or, equivalently, phase modulation. Other embodiments may generate a non-adiabatic pulse that is adjusted in at least one of amplitude modulation or phase modulation, accompanied by phase cycling of the pulse(s) by changing the phase of the saturation pulse through each of a cycle of different values for respective successive measurements.

The following discussion refers to formation analysis only for illustrative purposes. The disclosed embodiments may be used for cutting analysis and core analysis. For example, cutting or core analysis might be performed to monitor the composition, size, shape, color, texture, hydrocarbon content and other properties of drilling cuttings or core by a mud engineer or logger. The mud logger may capture samples of cuttings and/or cores for subsequent analysis and archiving.

FIG. 1 is a diagram showing an NMR tool 100, according to various examples of the disclosure. The NMR sensor tool 100 of FIG. 1 is for purposes of illustration only as the various examples disclosed herein may be used in other NMR tools. Reference to "downhole" is for purposes of brevity only. The NMR sensor tool 100 and any methods used herein may be performed within the drilled borehole, at the surface, and/or in a laboratory. Thus, "downhole" may refer to any of these scenarios.

Figure 19:
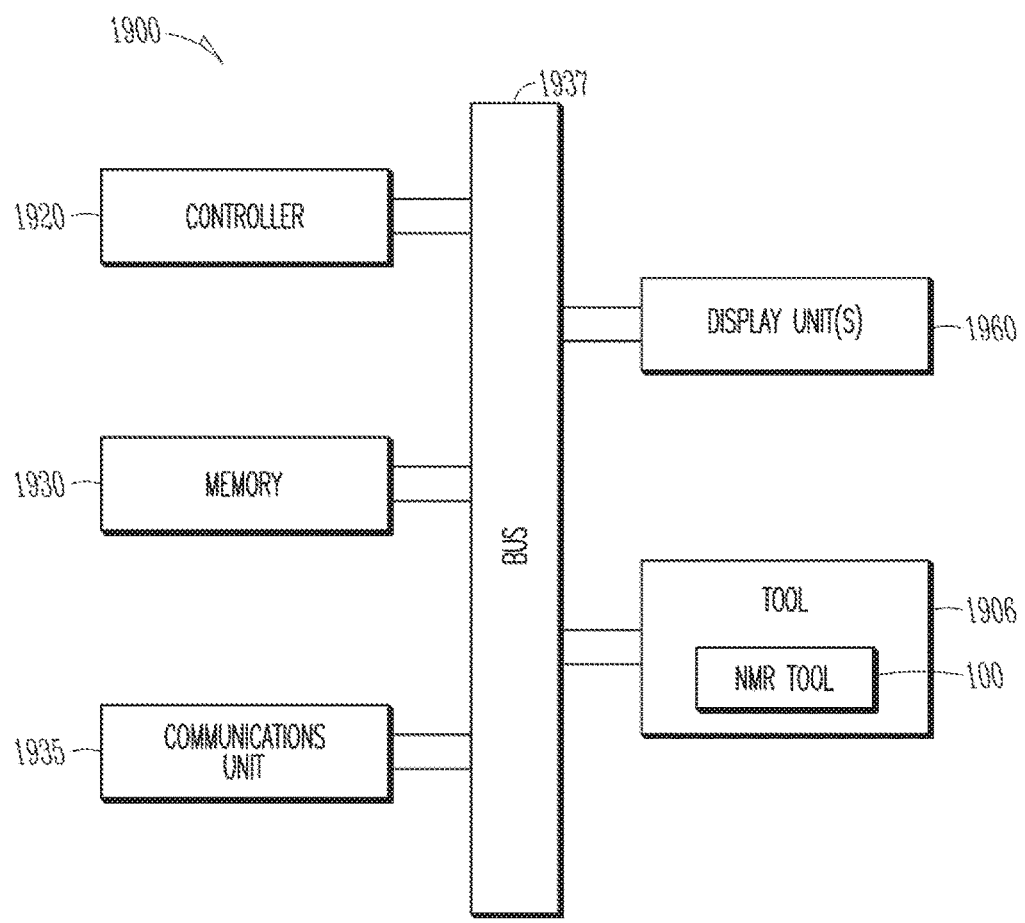
FIG. 19 is a block diagram of an example system operable to implement the activities of multiple methods, according to various examples of the disclosure.

The NMR tool 100 includes control circuitry 102 that provides NMR control parameters 112 to an NMR device 104. The control circuitry 102 directs the operations of the NMR device 104 (e.g., a downhole tool or laboratory equipment) by providing commands, programming, and/or data to the transmitter 108 of the NMR device 104 based on the NMR control parameters 112. The control circuitry 102 may take the form of a computer system as illustrated in FIG. 19 and discussed subsequently. Further, in some examples, the NMR control parameters 112 enable adjustment of pulse sequences and receiver window options based on a default configuration, user selection, and/or calibration.

In an example, the components of the NMR tool 100 may be located at the surface (e.g., as part of an NMR facility or laboratory) or downhole (e.g., as part of one or more logging tools). In other examples, some of the components (e.g., control circuitry 102) may be located at the surface while other components (e.g., NMR device 104) are located downhole.

The NMR device 104 includes a transmitter (TX) 108, a receiver (RX) 110, and NMR spectrometer components 106 for transmitting RF pulses and receiving NMR signals. The transmitter 108 may include, for example, a programmable pulse sequence device, a radio frequency (RF) synthesizer, a phase shifter, a pulse gate, an amplifier, and/or other components. The receiver 110 may include, for example, an analog-to-digital converter (ADC), filters, mixers, splitters, pre-amplifiers, and/or other components to receive magnetic resonance signals and recover measurement data. The magnetic resonance spectrometer components 106 may include one or more magnets, shim coils, probes/antennas, and/or field-frequency lock components. The magnetic resonance spectrometer components 106 may further include a duplexer that enables separation between transmission current and reception current.

The transmitter 108 of the NMR device 104 is configured to transmit signals (e.g., modulated saturation pulses). If the NMR device 104 is part of a downhole tool, the signals are transmitted into a geological formation in order to determine a composition of the formation.

The receiver 110 of the NMR device 104 is configured to receive and decode magnetic resonance signals (e.g., from a geological formation). If the NMR device 104 is part of a downhole tool, the received signals may comprise a reflected response from the geological formation (e.g., reservoir, volume to be measured). The raw NMR measurements or processed NMR data is output from the receiver 110 to the control circuitry 102 for storage, display, and/or analysis. In some embodiments, the control circuitry 102 may further process raw NMR measurements or processed NMR data received from the NMR device 104.

The NMR tool 100 may be used as part of the methods described herein to improve the accuracy and efficiency of the $T_1$ measurement in NMR logging. One aspect of some methods generates a pulse or train of pulses that are shaped (e.g., variation of RF amplitude during a single pulse) in such a way as to realize a saturation or inversion of the z component of the magnetization for the $T_1$ measurement in saturation recovery pulse sequence or inversion recovery pulse sequence, respectively.

The $T_1$ relaxation time is indicative of the characteristics of the geological formation being measured. For example, different types of formation and different types of fluids may result in different $T_1$ relaxation times during an NMR logging operation. Fluids, as used herein, may include liquids or gases.

The generated pulse or train of pulses from the NMR tool 100 may be adiabatic or non-adiabatic pulses that are shaped to provide a wide frequency bandwidth by using appropriate modulation functions for the AM, frequency modulation (FM) or phase modulation (PM). Such a pulse may use less RF peak amplitude to realize substantially uniform saturation or inversion of the nuclear spins over a wide bandwidth with high selectivity where available peak RF amplitude is limited. This may also extend the total logging time of a logging tool. Thus a saturation or inversion pulse may be considered optimized when it results in a substantially uniform saturation or inversion response from a formation (e.g., fluid) while using a minimum amount of RF energy (i.e., least amount of RF energy), where the minimum amount of RF energy is indicated by the result of Bloch's equations.

Calibration procedures may be used to adjust one or more of the pulse parameters (e.g., bandwidth, selectivity, pulse length, total RF energy consumption, amplitude and duration) of an adiabatic or non-adiabatic pulse to realize the saturation or inversion of the z component of the magnetization of the nuclear spins. Additionally, phase-cycling techniques may be used to suppress undesirable signals resulting from the gradient of the magnetic field at a bandwidth and inhomogeneity of the $B_1$ field.

Subsequent examples utilize Bloch's equations. As used herein Bloch's equations are a set of macroscopic equations that are used to calculate the nuclear magnetization $M=(M_x, M_y, M_z)$ as a function of time when relaxation times $T_1$ and $T_2$ are present (i.e., $T_1$=nuclear spin-lattice relaxation (relaxation in the z-direction), $T_2$=nuclear spin-spin relaxation (relaxation in the x-y plane)). Bloch's equations are considered macroscopic since they describe the equations of motion of macroscopic nuclear magnetization that can be obtained by summing up all nuclear magnetic moment in the sample.

Figure 2:
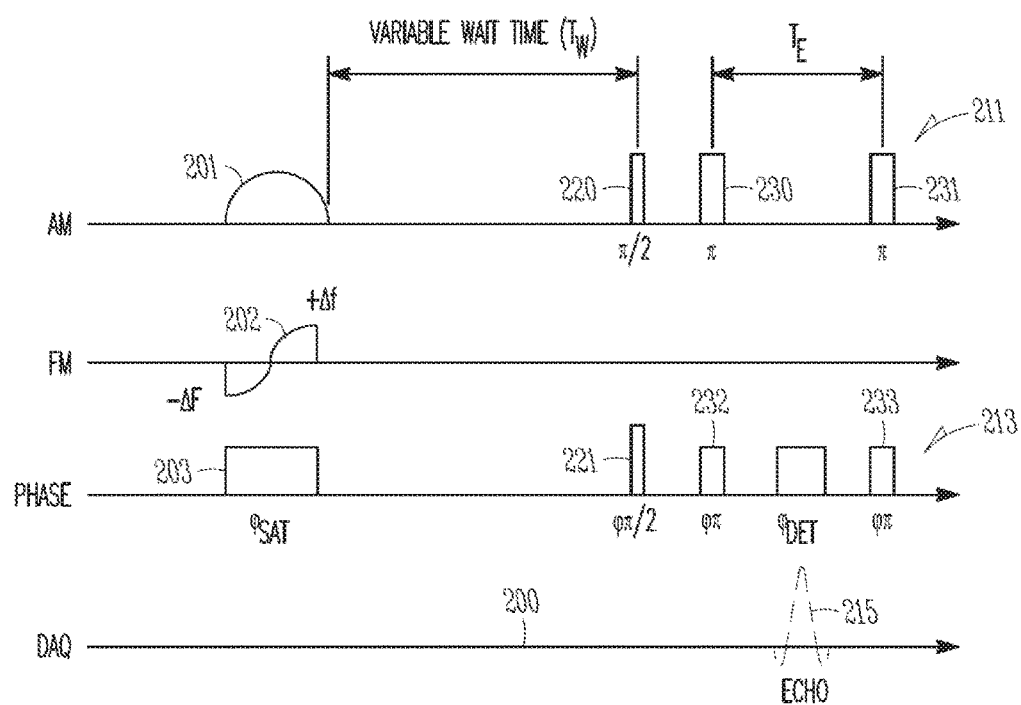
FIG. 2 is a plot of saturation pulses and readout pulses for transmission from the NMR tool, according to various examples of the disclosure.

FIG. 2 is a plot of saturation pulses and readout pulses for transmission from the NMR tool, according to various examples of the disclosure. For the purposes of brevity and clarity, the following discussion refers to the pulse 201-203 of FIG. 2 as a saturation pulse. However, the pulse 201-203 may be implemented as either a saturation pulse or an inversion pulse.

The plot of FIG. 2 illustrates a single or a plurality of saturation pulses that may use various modulations 201-203 and their respective readout sequences 211, 213 that may be transmitted by the NMR tool 100. As described subsequently, FIG. 2 also illustrates a resulting data acquisition line 200 (DAQ) comprising an echo signal 215 that may be received by the NMR tool 100 as a result of the readout pulse sequences 211, 213. The saturation pulses 201-203 and readout pulses 211, 213 are for purposes of illustration only. Other examples may include many different implementations of these pulses.

In the example of FIG. 2, the saturation pulse may be realized by one or more of AM pulses 201, FM pulses 202, and/or a PM pulse 203 transmitted by the NMR tool 100. The AM pulse 201 and/or the FM pulse 202 may also be realized by transmission of just the PM pulse 203.

The design of optimal amplitude, frequency/phase modulation may be accomplished in various ways. For example, simulations and/or experimentations may be used to design these types of modulation. The optimal adiabatic or non-adiabatic saturation pulse or pulses may be designed by adjusting one or more of amplitude, phase, frequency, amplitude modulation, phase modulation, or frequency modulation of the adiabatic pulse, such that a substantially uniform response is received from the formation while using a minimum amount of RF energy.

The saturation pulse 201-203 includes a pulse or a train of pulses that saturate or invert the polarized $M_z$ magnetization and readout sequence (e.g., Carr-Purcell-Meiboom-Gill (CPMG) where the nuclear spins are first flipped to a plane perpendicular to the static magnetic field direction using a tipping pulse followed by a series of refocusing pulses). For example, the fluid in a formation may be in a state of equilibrium. The saturation pulse 201-203 destroys that state of equilibrium, and the time it takes for the fluid to return to the state of equilibrium may be expressed as the $T_1$ time.

One or more of the pulse parameters (e.g., bandwidth, selectivity, pulse length, total RF energy consumption amplitude and duration) may be adjusted for one or more of the pulses 201-203 in order to optimize that particular saturation pulse in order to create a null state (i.e., zero nuclear spin state) in a reservoir of a formation. At the end of a saturation pulse or train of pulses, the $M_z$ magnetization component becomes zero within the bandwidth while the $M_x$ and $M_y$ magnetization components are non-zero—the resulting nuclear spin states are dependent on the type of modulation (e.g., AM, FM and PM) used for the saturation or inversion pulse.

The saturation pulse, once optimized for the formation, creates a broadband region in the formation that is in an initial, known state (i.e., null or zero spin state). A broadband RF pulse may be defined as a pulse that produces a wide range of spin isochromat components within the volume of interest (e.g., fluid) uniformly responding to the RF pulse. Such a broadband, highly volume-selective RF pulse may enable measurements of a well-defined section of fluid sample with minimal disturbance of the spins that are located outside of the section.

Various examples may vary the phase of the saturation pulse 201-203, the phases of the readout pulses 211, 213, the direction of the FM in a saturation pulse 201-203, and/or the wait time period $T_w$ in order to reduce undesirable signal contributions. For example, the phase of the saturation pulse 201-203 may be selected from $\varphi_{sat}=\{0, 90, 180, 270\}$ degrees; the direction of FM may be selected from a positive direction (i.e., $\{-\Delta f$ to $+\Delta f\}$) or a negative direction, (i.e., $\{+\Delta f$ to $-\Delta f\}$); the phase of the $\pi/2$ pulse 220, 221 and the phase of $\pi$ pulses 230-233 may be selected from $\{0, 90, 180, 270\}$; the variable wait time $T_w$ may be selected in a range from approximately 0.5 millisecond (ms)) to approximately 15000 ms.

An NMR signal 215 (i.e., echo) is detected by using a pulse sequence, such as CPMG, after the predetermined wait time $T_w$. A $\pi/2$ pulse 220, 221 from a monochromatic RF signal in readout sequence is calibrated for the on-resonance component of the magnetization to be rotated by 90° around the axis as defined by the phase of the $\pi/2$ pulse. However, since the net rotation of any off-resonance components is not equal to 90°, the off-resonance $M_x$ and $M_y$ magnetization components originated from the saturation pulse 201-203 may induce an undesirable signal within the data acquisition window. This may especially be true for NMR logging tools where spins are in the presence of significant gradient magnetic field. Since $M_x$ and $M_y$ magnetization components are dependent on the wait time $T_w$, and the modulation functions of the saturation pulse (i.e., direction of frequency modulation and phase of the saturation pulse) proper phase-cycling and the wait time $T_w$ may be used to reduce the signal contribution from this undesirable coherence. This may improve the signal averaging, thus improving the SNR per unit time.

Figure 3:
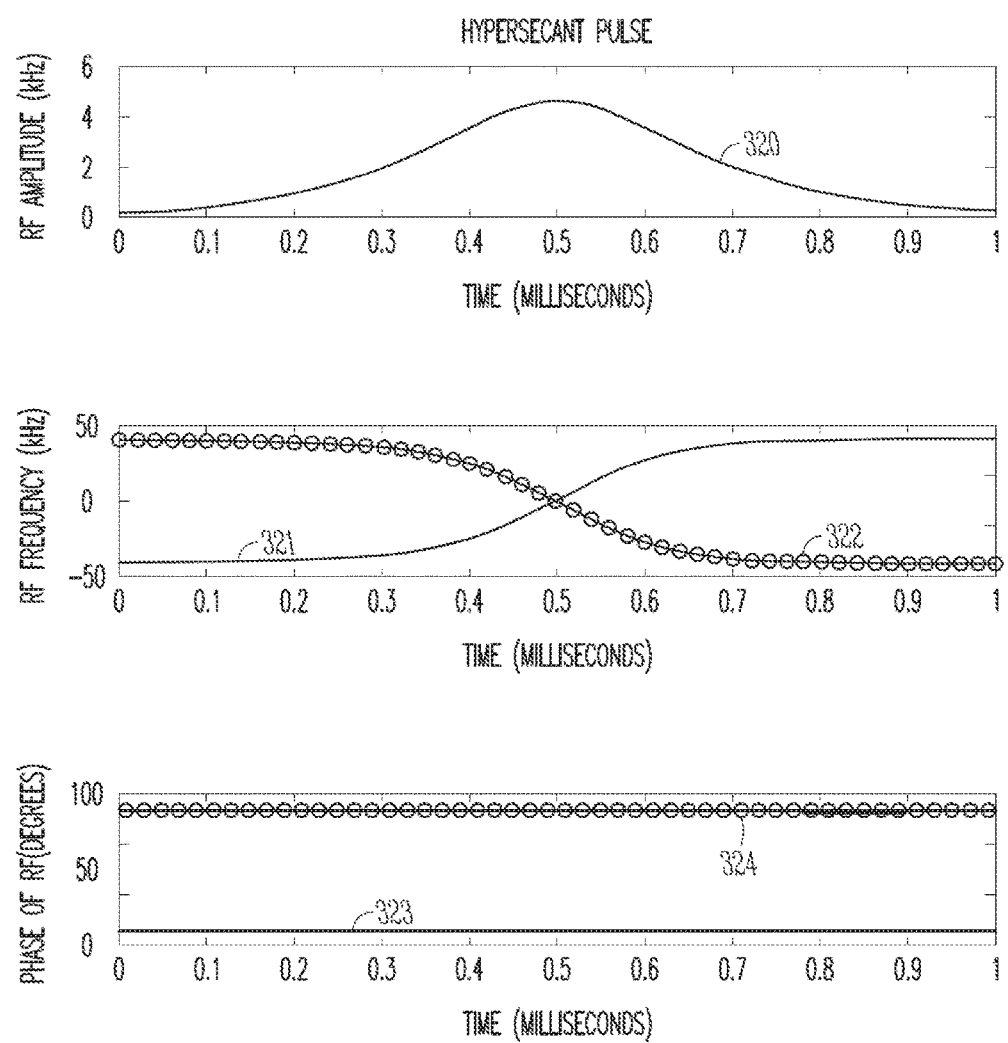
FIG. 3 is a plot of a representative modulation scheme of the saturation pulse, according to various examples of the disclosure.

FIG. 3 is a plot of a representative modulation scheme of the saturation pulse signals, according to various examples of the disclosure. The modulation scheme illustrated in FIG. 3 is a hyperbolic secant (HS) function modulated adiabatic pulse. This modulation scheme is for purposes of illustration only as other types of modulation may be used.

The modulated pulse of FIG. 3, when transmitted into a geological formation, may produce the saturation or inversion of the polarized nuclear spins. Depending on the various limiting factors such as peak RF power, total RF energy consumption, frequency selectivity, bandwidth, and/or pulse time, the optimized saturation pulse that produces the polarized nuclear spins may be determined by using various modulation functions for AM, FM and/or PM modulations.

In one example, curve 320 shows the modulation function for the amplitude modulation of the HS adiabatic pulse. Curves 321 and 322 show the modulation function for frequency modulation, with positive modulation direction (curve 321) and negative modulation direction (curve 322), of the HS adiabatic pulse. The HS adiabatic pulse realizes substantially uniform saturation of the $M_z$ magnetization component over a wide bandwidth that is determined by a range of frequency sweep. Curve 323 and curve 324 show the phase of the saturation pulse. This phase cycling scheme is for purposes of illustration only as other types of phase cycling may be used.

As used herein phase cycling may be defined as changing the phase used for the saturation pulse (and/or pulses in the readout pulse sequence) through a cycle of different values for successive measurements. For example, a first measurement may transmit a saturation pulse (and/or readout pulses) for a first measurement using a first phase. A second measurement may transmit a saturation pulse (and/or readout pulses) for a second measurement using a second phase.

Figure 4:
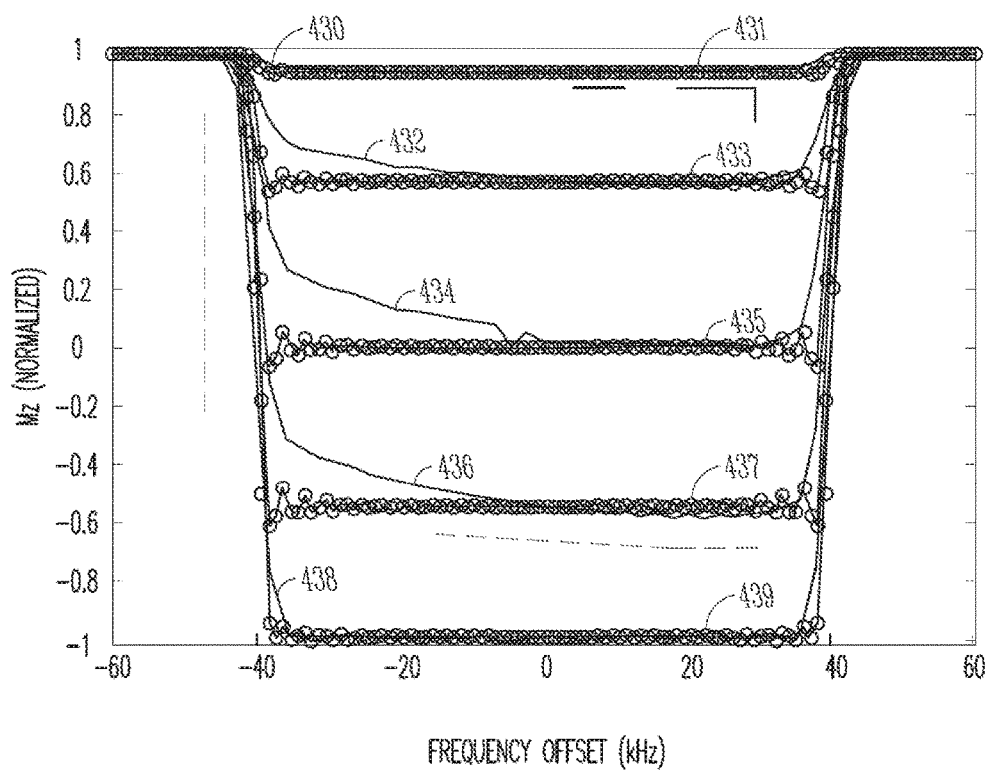
FIG. 4 is a plot of simulation and experimentation results of resultant $M_z$ magnetization component resulting from the saturation pulse signals, according to various examples of the disclosure.

FIG. 4 is a plot of simulation and experimentation results of resultant $M_z$ magnetization component resulting from the saturation pulse, according to various examples of the disclosure. The plotted results show the resultant $M_z$ magnetization component, kilohertz (kHz), of proton spins measured shortly after the HS adiabatic pulse (see FIG. 3) at various $B_1$ amplitudes (i.e., RF peak). The simulation results are illustrated by the plots having dashed lines with circles and the experimental results are illustrated by the plots with solid lines.

Curves 430 and 431 illustrate the normalized $M_z$ magnetization component of nuclear spin after the HS adiabatic pulse with $B_1$ (i.e. RF peak amplitude) of 1.0 kHz. Curves 432 and 433 illustrate the normalized $M_z$ magnetization component of nuclear spin after the HS adiabatic pulse with $B_1$ (i.e. RF peak amplitude) of 2.7 kHz. Curves 434 and 435 illustrate the normalized $M_z$ magnetization component of nuclear spin after the HS adiabatic pulse with $B_1$ (i.e. RF peak amplitude) of 4.5 kHz. Curves 436 and 437 illustrate the normalized $M_z$ magnetization component of spin after the HS adiabatic pulse with $B_1$ (i.e. RF peak amplitude) of 6.6 kHz. Curves 438 and 439 illustrate the normalized $M_z$ magnetization component of spin after the HS adiabatic pulse with $B_1$ (i.e. RF peak amplitude) of 12.2 kHz.

The curves 430-439 illustrated in FIG. 4 show that the effective bandwidth of the pulse is about 80 kHz, which agrees with the range of the FM pulse, defined in the HS adiabatic pulse shown in FIG. 3. The curves 430-439 of FIG. 4 show that the responses of the spins are substantially uniform over the bandwidth. Slopes appearing in the experimental data (i.e., curves 430, 432, 434 and 436) are due to instrument artifacts. The curves 430-439 show that the HS adiabatic pulse has high selectivity, such that the $M_z$ magnetization component outside of the bandwidth of the pulse is not perturbed by the HS adiabatic pulse, and a sharp transition between the perturbed spins and unperturbed spins is created.

Figure 5:
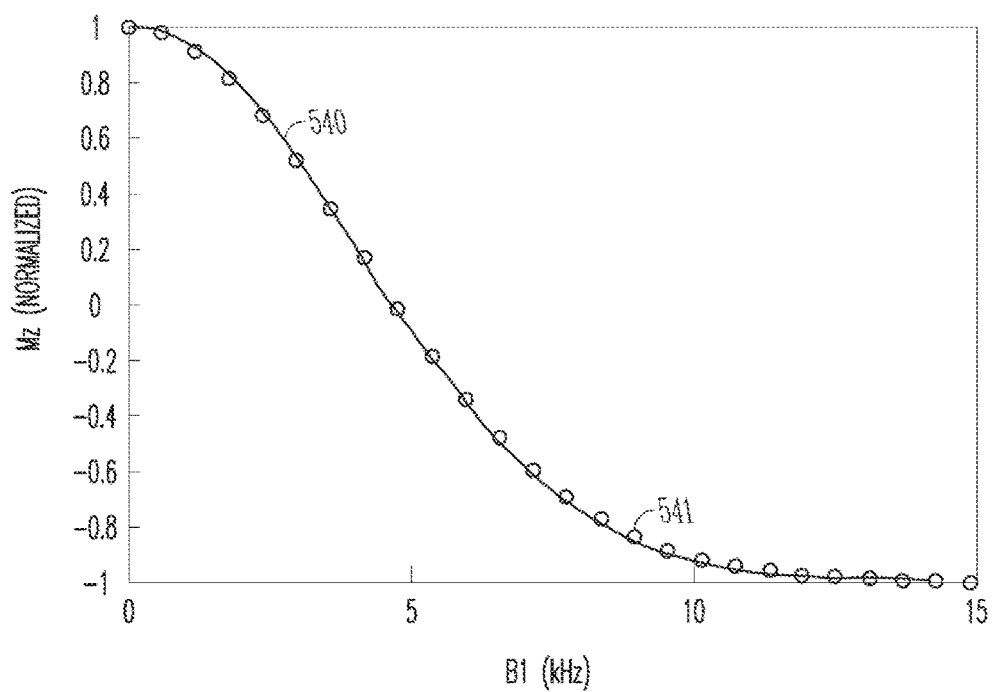
FIG. 5 is a plot of simulation and experimentation results of the $M_z$ magnetization component as a function of peak RF amplitude, according to various examples of the disclosure.

FIG. 5 is a plot of simulation and experimentation results of the $M_z$ magnetization component as a function of peak RF amplitude, according to various examples of the disclosure. This plot shows the response of the nuclear spin as a function of amplitude of the saturation pulse. In this example, the simulation results are indicated by circles (i.e., curve 541) while the experimental results are indicated by a line (i.e., curve 540). These plots show the $M_z$ magnetization component as a function of the peak RF amplitude after the HS adiabatic pulse.

The coincident curves 540, 541 show that there is a match between the experimental data and the simulation data. This confirms that the optimal peak amplitude of an adiabatic saturation pulse may be theoretically found by solving the Bloch's equations for given parameters, such as duration of the RF pulse, range of the frequency sweep, functional forms of the AM, FM or PM.

In a conventional method, time-consuming calibration procedures are used to find an optimal amplitude of the saturation pulse that may nullify or invert the $M_z$ magnetization. For example, in one conventional implementation, the optimal amplitude of the saturation pulse is theoretically found for a given modulation function. Then, after calibration of the readout sequence (e.g., CPMG sequence to optimize the peak RF amplitude for the NMR signal detection), the optimal peak RF amplitude of the saturation/inversion pulse is analytically determined from the proportionality that is found from the Bloch's equation solution for a given adiabatic pulse.

Figure 6:
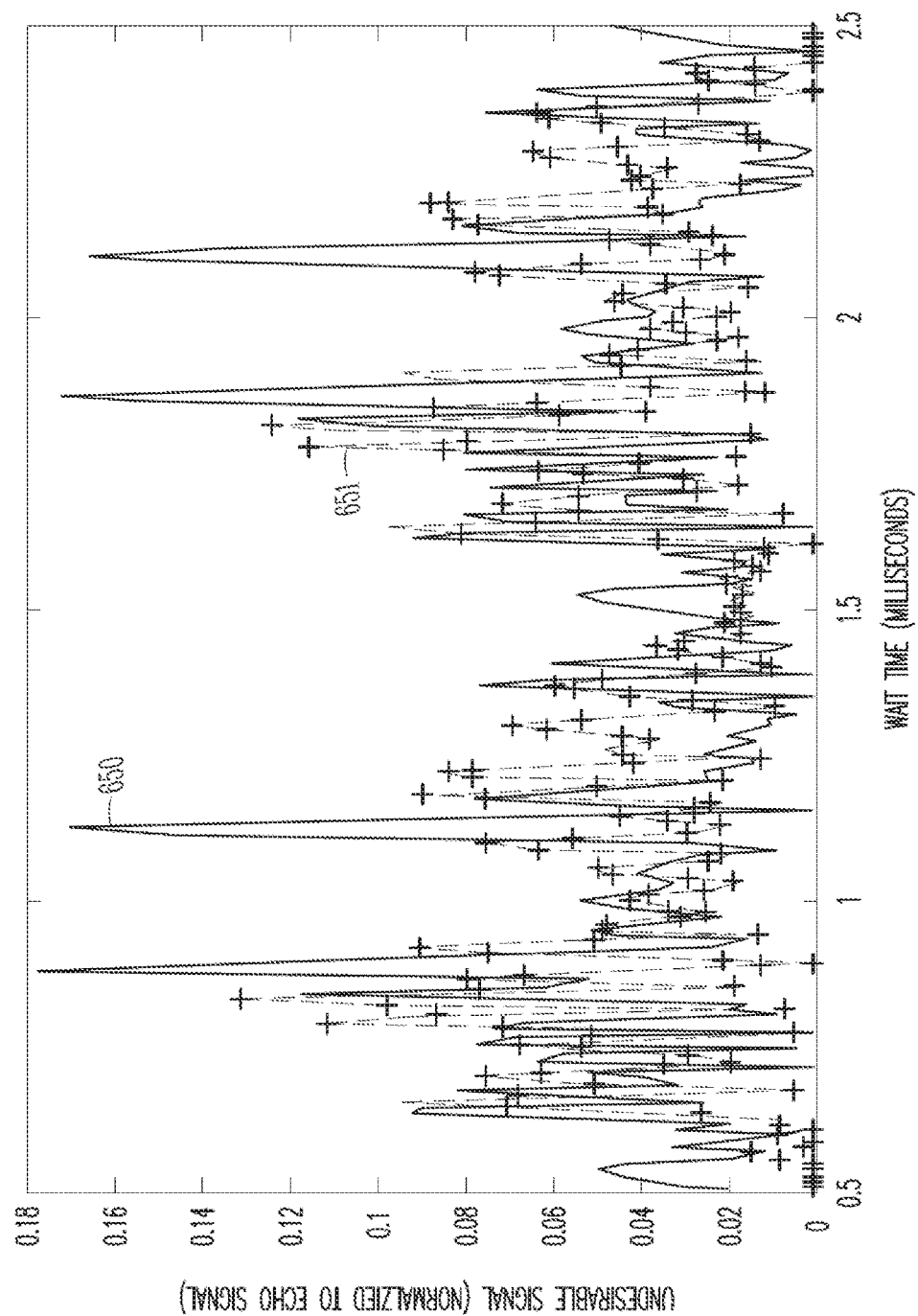
FIG. 6 is a plot of simulation results of an undesirable signal originating from the $M_x$, $M_y$ magnetization components after the saturation pulse, according to various examples of the disclosure.

FIG. 6 is a plot of simulation results of an undesirable signal originating from the $M_x$, $M_y$ magnetization components after the saturation pulse, according to various examples of the disclosure. These plots have been normalized to the maximum echo signal in the absence of the saturation pulse. The plots originated from the $M_x$, $M_y$ components after the HS saturation pulse, as a function of the wait time $T_w$, detected by the readout sequence within the data acquisition window.

Curve 650 (marked as a line) shows the simulation results of the undesirable signal when the phase of the saturation pulse and the readout pulse are composed of $AM_{270}$-$FM_p$-$(\pi/2)_{270}$-$\pi_0$, where subscript 'p' represents the positive direction of the FM in the saturation pulse and subscripts '270' and '0' represent the phase of their respective pulses.

Curve 651 (marked as dashed line with crosses) shows the simulation results of the undesirable signal when the phase of the saturation pulse and the readout pulse are composed of $AM_0$-$FM_n$-$(\pi/2)_{270}$-$\pi_0$, where subscript 'n' represents the negative direction of the FM in the saturation pulse and subscripts '270' and '0' represent the phase of the respective pulse.

The plots 650, 651 of FIG. 6 show that the undesirable signal depends on the phase of the saturation pulse and the direction of the frequency modulation. It also shows that the undesirable signal depends on the variable wait time $T_w$. In one implementation, phase-cycling combination and appropriate wait times are selected such that the undesirable noise signal detected within the data acquisition window in the readout sequence is effectively suppressed. This may improve the signal-to-noise ratio (SNR) per unit time in some examples.

In another embodiment, a non-adiabatic pulse (e.g., sinc pulse) may be used as a saturation pulse. In general, a bandwidth of a single monochromatic pulse is inversely proportional to the duration of the pulse, which is also accompanied by undesirable infinite number of side lobes that may perturb the spins in unwanted regions. However, a non-adiabatic pulse in the time domain whose frequency is constant can have a uniform frequency response over a specified bandwidth.

A non-adiabatic pulse may be shorter than an adiabatic pulse. For example, a hypersecant pulse (e.g., adiabatic pulse) may have a duration of approximately 1 ms while a sinc pulse (e.g., non-adiabatic pulse) may have a duration of approximately 200 µs. Since one of the motivations for using saturation pulses is to improve accuracy for measurement of short NMR relaxation times, including relaxation times that are less than 1 ms, the shorter duration of the non-adiabatic pulse may be beneficial in certain embodiments.

One aspect of the disclosure is that the non-adiabatic pulse at a constant frequency is optimized to provide wide frequency bandwidth by using appropriate amplitude modulation (AM). The non-adiabatic pulse realizes uniform saturation or inversion of the spins over a specified bandwidth with high selectivity and simplifies calibration procedures to optimize the amplitude of the non-adiabatic pulse to realize the saturation or inversion of the z component of the magnetization of the spins ($M_z$). A phase-cycling technique may be used to suppress any undesirable signal due to the gradient of the magnetic field. At the end of a saturation pulse, the $M_z$ magnetization component becomes zero within the bandwidth. On the other hand, the $M_x$ and $M_y$ magnetization components are non-zero and spin states depend on the modulations of the saturation pulse.

The NMR signal is detected by using a readout pulse sequence, such as a CPMG sequence, after the predetermined wait time $T_w$ (see FIG. 2, for example) between the saturation pulse (or last pulse of a train of saturation pulses). A typical 'A' pulse, using a monochromatic RF signal, is calibrated for the on-resonance component of the magnetization to be rotated by 90 degrees around the axis defined by the phase of an excitation pulse. However, the net rotation of any off-resonance components is not equal to 90°, therefore any off-resonance $M_x$ and $M_y$ magnetization components originating from the saturation pulse may induce undesirable signals within the data acquisition window. This may be especially true for NMR logging tools where spins are in the presence of significant gradient magnetic field. Since $M_x$ and $M_y$ magnetization components are dependent on the wait time $T_w$ and the modulation and phase of the saturation pulse, proper phase-cycling and the wait time can be used to minimize the signal contribution from this undesirable coherence. This may improve the signal averaging that may improve the SNR per unit time.

Figure 7:
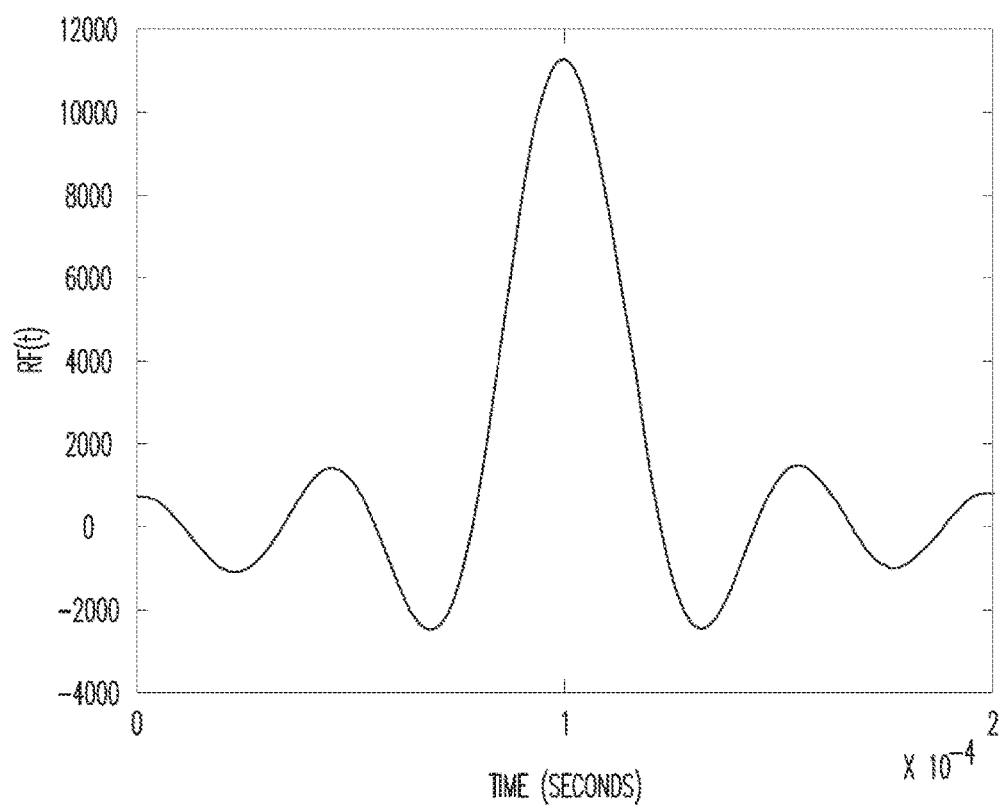
FIG. 7 is a plot of a representative modulation scheme for a non-adiabatic saturation pulse, according to various examples of the disclosure.

FIG. 7 is a plot of a representative modulation scheme (e.g., sinc pulse) for a non-adiabatic saturation pulse, according to various examples of the disclosure. This figure shows amplitude modulation of a saturation pulse to realize the saturation or inversion of the polarized spin states. For purposes of illustration only, the curve shows the modulation function for amplitude modulation. Other forms of modulation may also be used to generate a non-adiabatic saturation pulse. The sinc pulse of FIG. 7 realizes uniform saturation of the $M_z$ magnetization component over a wide bandwidth, which is determined by the parameters such as pulse length, number of lobes, and peak RF amplitude.

Figure 8:
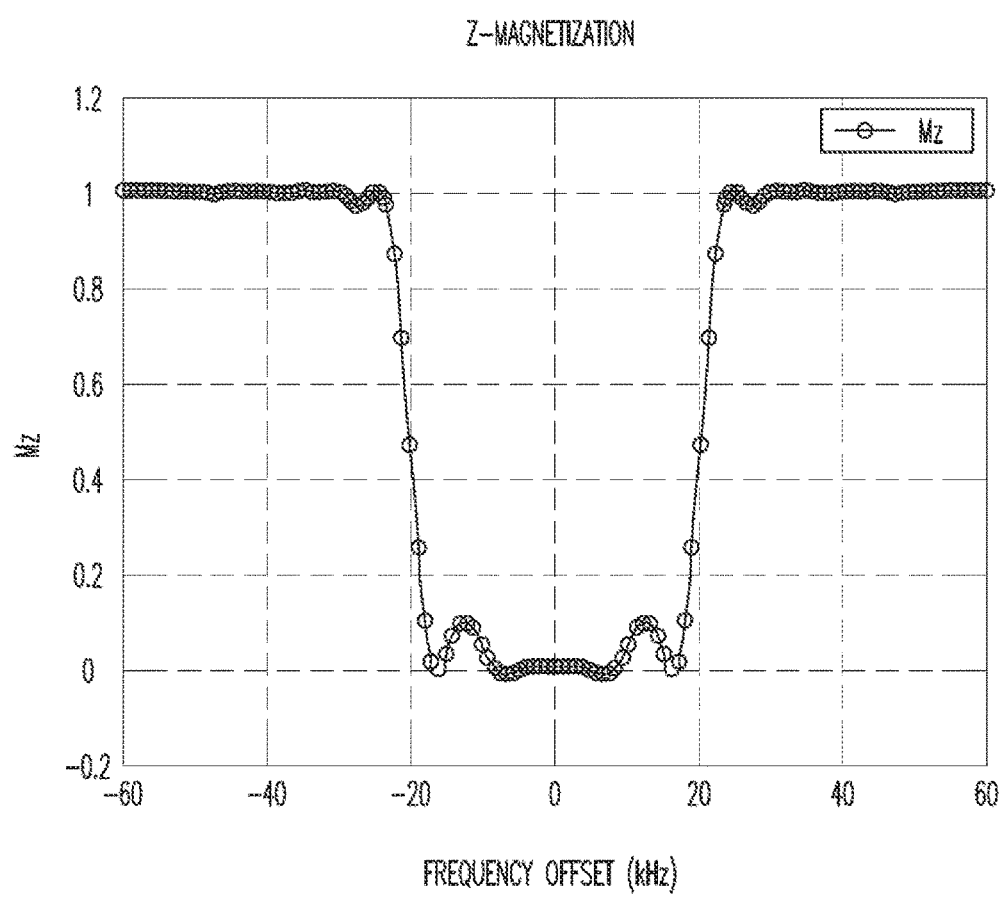
FIG. 8 is a plot of a simulation result of the resultant $M_z$ magnetization component resulting from the non-adiabatic pulse, according to various examples of the disclosure.

FIG. 8 is a plot of a simulation result of the resultant $M_z$ magnetization component resulting from the non-adiabatic pulse, according to various examples of the disclosure. The plot of FIG. 8 is the normalized $M_z$ magnetization component of spin relatively shortly after a sinc pulse has been transmitted into the geological formation as a non-adiabatic saturation pulse.

Figure 9:
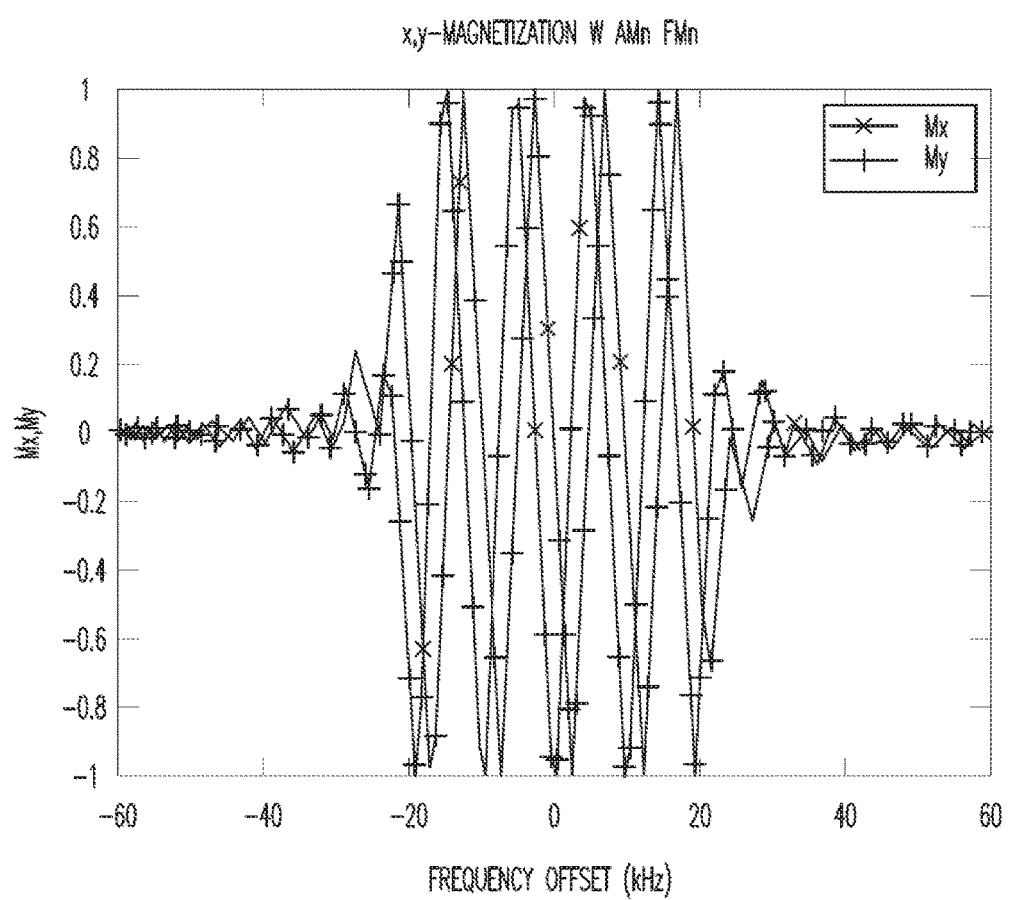
FIG. 9 is a plot of a simulation result of the resultant $M_x$ and $M_y$ magnetization components from the non-adiabatic saturation pulse, according to various examples of the disclosure.

FIG. 9 is a plot of a simulation result of the resultant $M_x$ and $M_y$ magnetization components from the non-adiabatic saturation pulse, according to various examples of the disclosure. The illustrated $M_x$ and $M_y$ plots are the normalized $M_x$ and $M_y$ magnetization components of spins shortly after the sinc pulse has been transmitted into the geological formation as the non-adiabatic saturation pulse.

The illustrated curves in FIGS. 8 and 9 show that the effective bandwidth of the saturation pulse is 40 kHz and that that the responses of the spins are uniform over the bandwidth. The illustrated curves in FIGS. 8 and 9 also show that the sinc pulse has high selectivity as a saturation pulse. For example, it can be seen that the $M_z$ magnetization component outside of the bandwidth of the pulse is not perturbed by the sinc pulse and a sharp transition exits between the perturbed spins and unperturbed spins.

Figure 10:
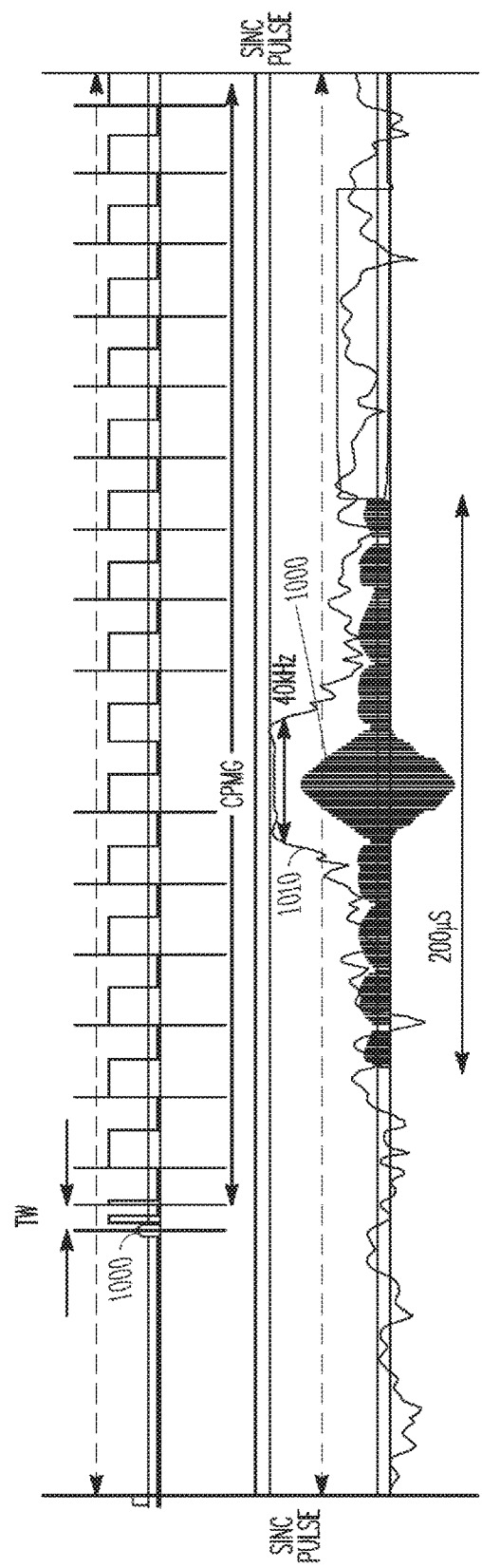
FIG. 10 is a plot of saturation experiments using a sinc pulse as the saturation pulse, according to various examples of the disclosure.

FIG. 10 is a plot of saturation experiments using a sinc pulse 1000 as the saturation pulse, according to various examples of the disclosure. The sinc pulse 1000 is shown having a duration of 0.2 ms for purposes of illustration only.

Other embodiments may use different pulse durations. The CPMG pulse sequence is used to detect the resultant $M_z$ magnetization component after a fixed wait time $T_w$ (e.g., 234 µs). This wait time is also for purposes of illustration only. The effective bandwidth of the sinc pulse is 40 kHz as shown by the frequency spectrum of the sinc pulse 1010.

Figure 11:
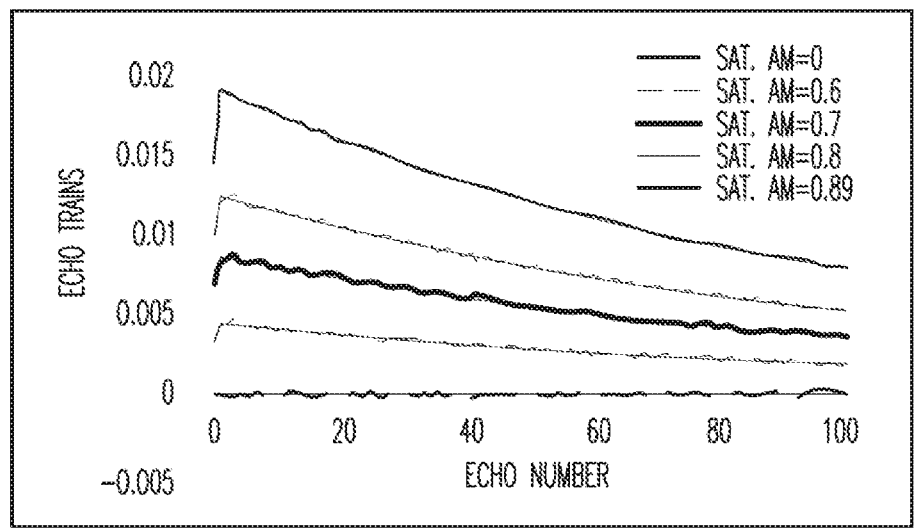
FIG. 11 are plots of echo trains resulting from the sinc pulse of FIG. 10 using various saturation pulse amplitudes, according to various examples of the disclosure.

FIG. 11 are plots of echo trains resulting from the sinc pulse of FIG. 10 using various amplitude modulation indices, according to various examples of the disclosure. This figures illustrates that, with a fixed wait time, the amplitudes of the echo train are proportional to the amplitude of the sinc pulse.

As one example, with a saturation pulse having an amplitude AMP=0.89, the amplitude of each echo train becomes zero. This demonstrates that the sinc pulse can be used to achieve saturation of spins over a selected frequency band. The optimal peak amplitude of a sinc pulse to achieve saturation can be analytically found by solving the Bloch's equations for given parameters, such as duration of the RF pulse length, bandwidth of pulse, or truncation of the sinc function.

Figure 12:
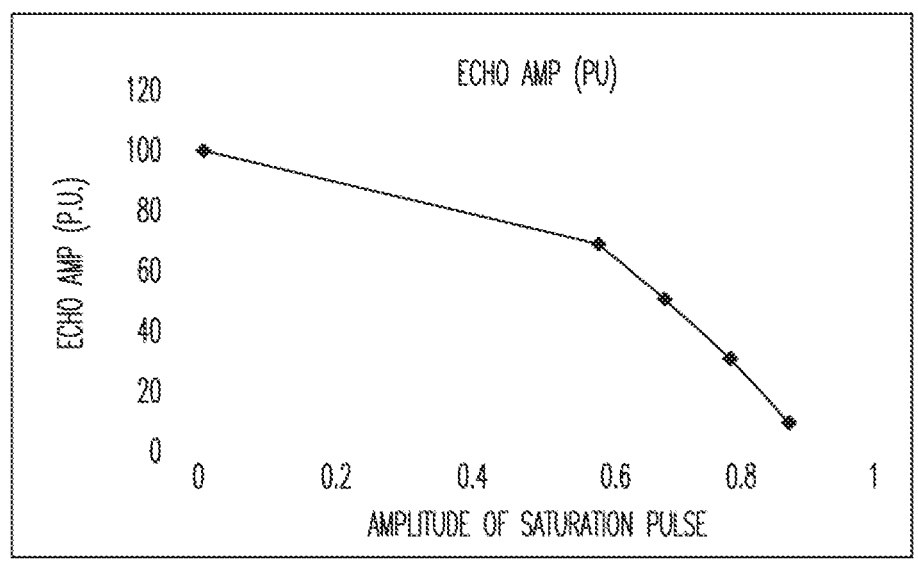
FIG. 12 is a plot of echo train amplitudes versus saturation pulse amplitude resulting from the sinc pulse of FIG. 10, according to various examples of the disclosure.

FIG. 12 is a plot of echo train amplitudes versus saturation pulse amplitude resulting from the sinc pulse of FIG. 10, according to various examples of the disclosure. After the calibration of the readout sequence (e.g., CPMG sequence) to optimize the peak RF amplitude for the NMR signal detection, an optimal peak RF amplitude of the saturation/inversion pulse may be determined from the proportionality found by solving the Bloch's equation solution for a given non-adiabatic pulse.

Figure 13:
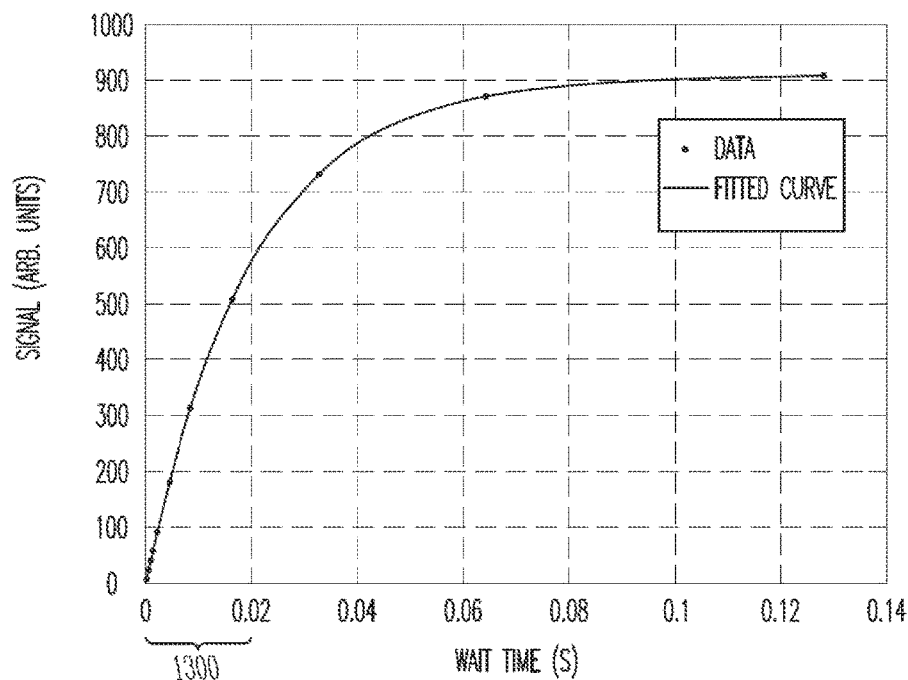
FIG. 13 is a plot of wait time $T_w$ versus signal showing a fit of an exponential curve to plotted simulation data, according to various examples of the disclosure.

FIG. 13 is a plot of wait time $T_w$ versus signal showing a fit of an exponential curve to plotted simulation data, according to various examples of the disclosure. A more detailed portion of this plot 1300 is illustrated in greater detail in FIG. 14.

FIG. 13 shows, through simulation output results, that phase cycling may be used to remove errors introduced into the $T_1$ measurement by undesirable $M_x$ and $M_y$ magnetization components generated by the sinc pulse used as a saturation pulse. In the plotted simulation, $T_1=T_2=20$ ms. A 300 µs sinc pulse with two-step phase cycling was used in the simulation to saturate the magnetization, and a CPMG sequence was used for echo readout.

FIG. 13 shows that a single decaying exponential curve is fit to the plotted data from the simulation results with a near perfect fit. This fit provides an indication that the saturation pulse is operating properly. The $T_1$ time constant found by the fit is 20.0 ms.

Figure 14:
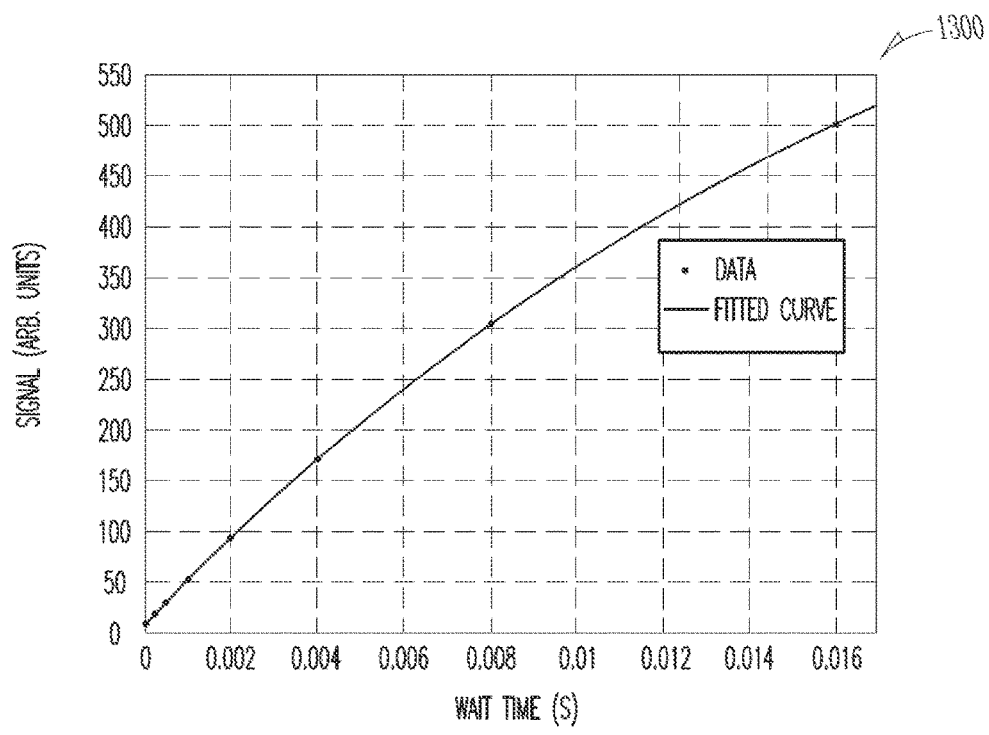
FIG. 14 is a more detailed plot of the wait time $T_w$ versus the signal plot of FIG. 13, according to various examples of the disclosure.

FIG. 14 is a more detailed plot of the wait time $T_w$ versus the signal plot of FIG. 13, according to various examples of the disclosure. As can be seen by the wait time units, this figure is a more detailed representation of a portion 1300 of the plot of FIG. 13. From the zoomed-in plot of FIG. 14, it can be seen that the phase cycle results in an accurate fit to the decaying exponential curve even for very short wait times. Also, the fact that the fit is not perfect (i.e., the plotted data does not go exactly to zero) is an indication of the plausibility of the simulation results since small imperfections are expected from a fit of a theoretical curve to simulation data.

Figure 15:
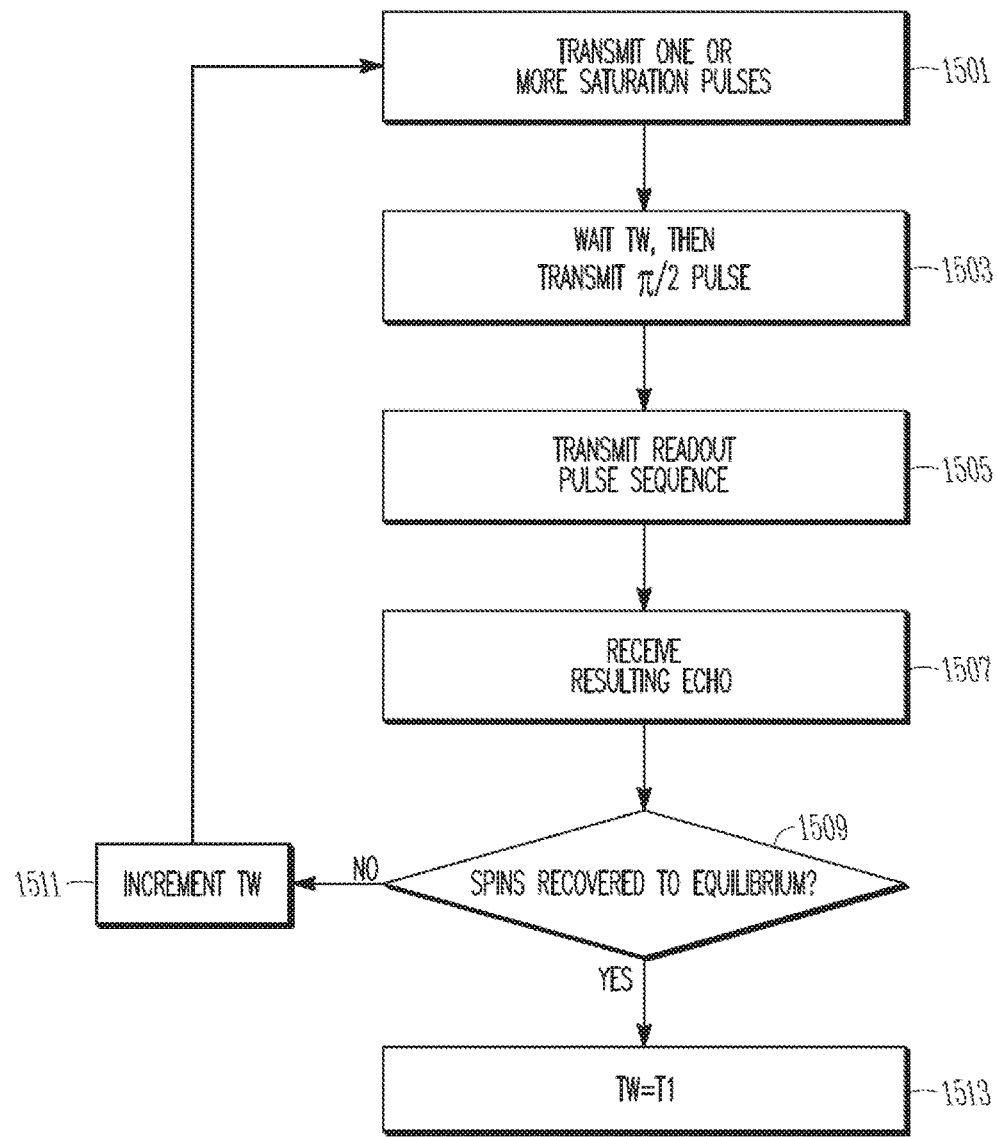
FIG. 15 is a flowchart of a method for shaping of a saturation pulse, according to various examples of the disclosure.

FIG. 15 is a flowchart of a method for using a saturation pulse, according to various examples of the disclosure. Reference is made to the pulse plots of FIG. 2 in the description of this method. This method may be performed in a simulation, in a downhole environment, or a combination of a simulation and downhole. For example, the pulses may be transmitted into a geological formation by the NMR tool 100 and an echo received from the formation by the NMR tool 100, the transmission of pulses and receipt of the echo may be performed as a simulation, or the transmission of the pulses and receipt of the echo may include a simulation for one or more initial executions of the method and then subsequent executions performed in a downhole environment.

In block 1501, one or more modified saturation pulses 201-203 (e.g., adiabatic, non-adiabatic) are transmitted into an object in order to measure the characteristics of the object (e.g., reservoir fluid). In block 1503, after a first predetermined wait time $T_w$, a pulse 220, 221 (e.g., $\pi/2$, whose phase is defined by $\varphi\pi/2$) is transmitted in order to transition the nuclear spins from the $M_z$ plane to the $M_x$ and $M_y$ plane. In block 1505, a recovery pulse sequence 230, 232 (e.g., $\pi$, whose phase is defined by $\varphi_\pi$) is then transmitted. In block 1507, a resulting echo response 215 is then received. In block 1509, it may then be determined from the received echo response whether, or to what percentage, the nuclear spins have recovered to equilibrium. In block 1511, if the spins have not recovered to equilibrium, the variable wait time $T_w$ is incremented and the process is repeated until the nuclear spins have recovered to equilibrium. In block 1515, the wait time $T_w$ is now equal to the $T_1$ relaxation time and, thus, an indication of the characteristics of the formation fluid.

Figure 16:
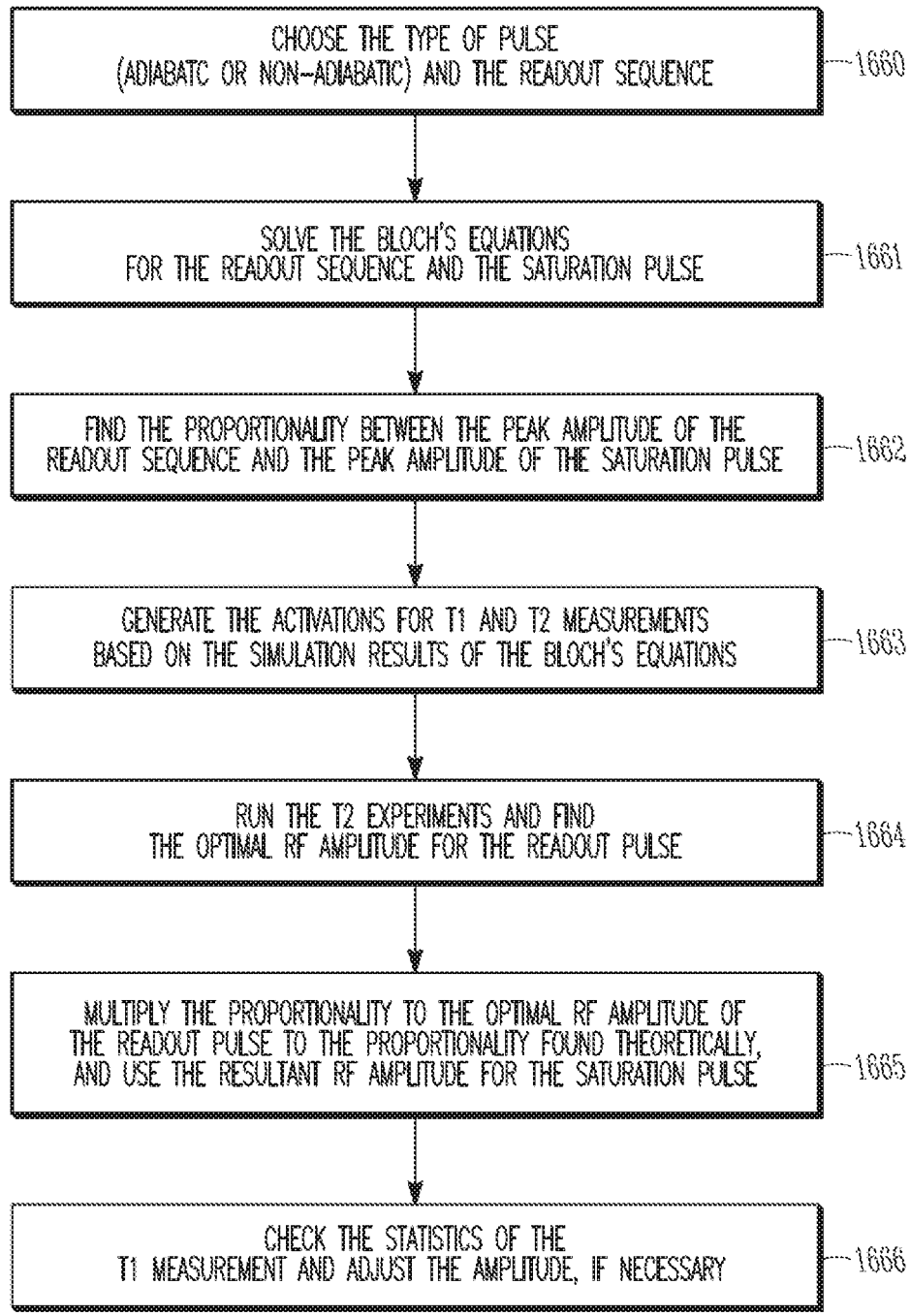
FIG. 16 is a flowchart of a method for saturation pulse calibration, according to various examples of the disclosure.

FIG. 16 is a flowchart of a method for calibration of the saturation pulses, according to various examples of the disclosure. Such a calibration method may be used to improve calibration of the adjustment of the pulse parameters for the saturation pulses in order to shape the pulse for transmission.

In block 1660, a type of adiabatic saturation pulse and its associated readout pulse sequence is chosen. For an initial execution of the calibration procedure without any initial measurement data on which to base a selection, the type of saturation pulse (e.g., adiabatic, non-adiabatic) and associated readout pulse sequence may be chosen based on theoretical assignment. The choice of pulse with a pulse length, shape and/or type of modulation can be performed according to the goal of the optimization. For example, one type of pulse may use a smaller RF peak amplitude or another type of pulse may use less RF energy. Thus, the initial pulse may be selected according to the optimization goal.

In block 1661, Bloch's equations are solved for the readout sequence and the saturation pulse in order to determine a desired amplitude for the pulse given the pulse shape. In block 1662, the proportionality between the peak amplitude of the readout pulse sequence and the peak amplitude of the saturation pulse is determined. In block 1663, activations for $T_1$ and $T_2$ measurements, based on the simulation results of the Bloch's equations from block 1661, are determined. In block 1664, $T_2$ experiments are executed to find the optimal RF amplitude for the readout pulse sequence. In block 1665, the proportionality to the optimal RF amplitude of the readout pulse sequence is multiplied with the proportionality found theoretically as discussed subsequently. The resultant RF amplitude is then used for the adiabatic saturation pulse. In block 1666, the statistics of the $T_1$ measurement may then be checked and the amplitude adjusted if desired.

In determining the proportionality theoretically, a readout sequence may be selected from a single spin echo sequence or a CPMG sequence where a train of $\pi$ pulses are applied, and a train of echoes are detected from each $\pi$ pulse. Once the readout sequence is selected, in a first step, pulse parameters such as shape or pulse length can be selected. In a second step, with the selected readout pulse, an evolution of spins may be found by solving the Bloch's equations. By adjusting the strength of the time-varying magnetic field (B1), which is often expressed in kHz, one can find the optimal B1 field strength of the readout pulse sequence. In a third step, the adiabatic pulse may then be introduced to achieve saturation or inversion for given pulse parameters, such as modulation type, modulation function, pulse length, and phase. The Bloch's equations may then be solved to find the optimal B1 amplitude of the selected adiabatic pulse in order to achieve saturation or inversion of the nuclear spins. This optimal B1 is often expressed in kHz.

In a fourth step, the following expression may be executed: A:B=C:D, where A is the optimal B1 amplitude of the readout sequence found in the second step and B is the optimal B1 amplitude of the saturation pulse determined in the third step. In a fifth step, $T_2$ experiments may be run using the pulse parameters that were selected in the first and second steps. In a sixth step, the RF amplitude (often expressed as kV) of the NMR logging tool may be adjusted to achieve a maximum echo signal for a given readout pulse sequence. An optimal RF voltage for the readout sequence may be assigned as 'C' in the expression in the fourth step.

In a seventh step, the optimal RF voltage for the choice of saturation pulse may be found from the above expression (i.e., C=(B/A)*C). For example, if A=10 kHz, B=3 kHz, C=1.2 kV, then, D=0.36 kV. In this example, the proportionality is B/A (i.e., 0.3). In an eighth step, the $T_1$ experiments are executed using the choice of saturation pulse minimum wait time ($T_w$) between the saturation pulse and the readout sequence, and the statistics checked to determine if it gives the minimum signal from the readout signal.

Figure 17:
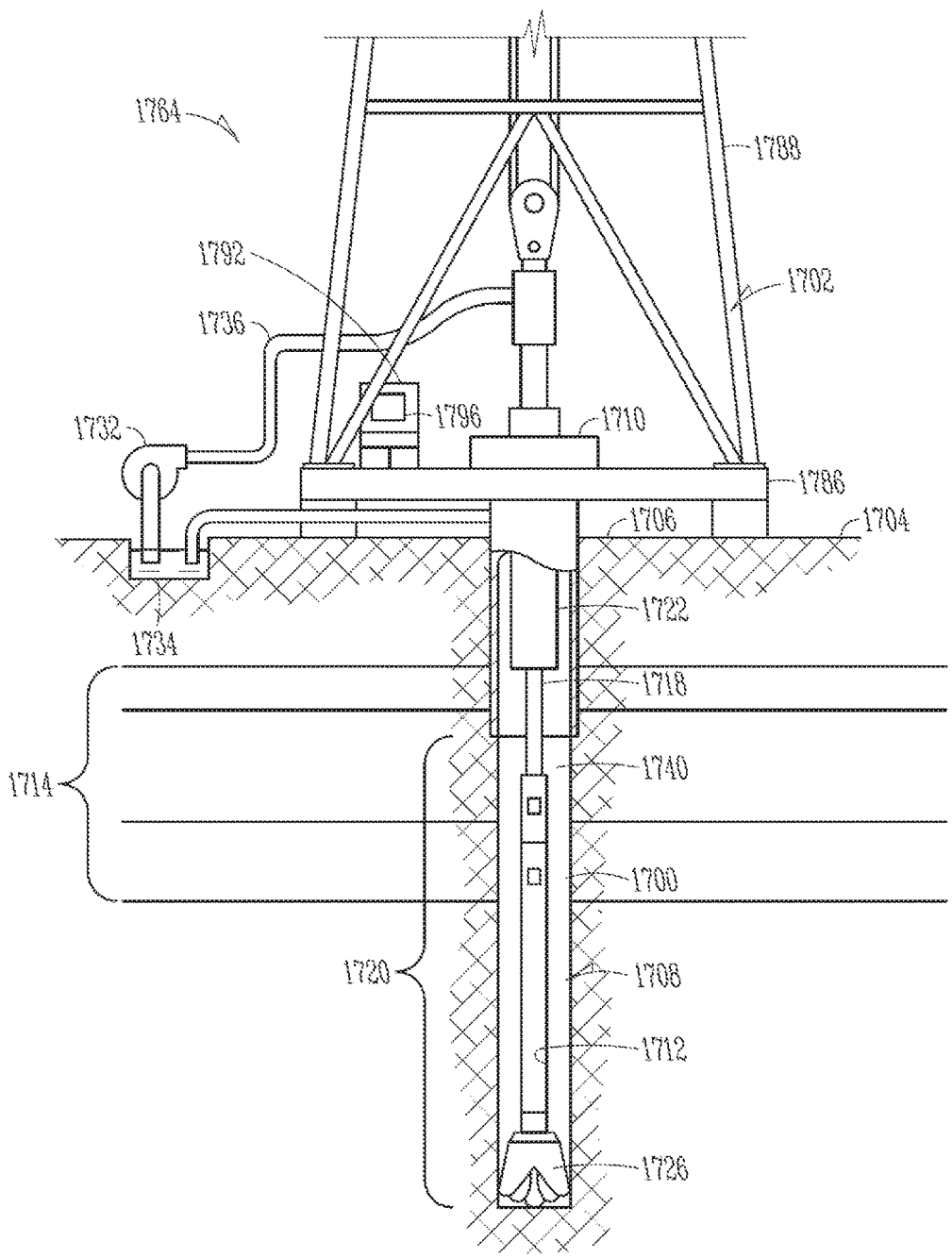
FIG. 17 is a diagram showing a drilling system, according to various examples of the disclosure.

FIG. 17 is a diagram showing a drilling system 1764, according to various examples of the disclosure. The system 1764 includes a drilling rig 1702 located at the surface 1704 of a well 1706. The drilling rig 1702 may provide support for a drillstring 1708. The drillstring 1708 may operate to penetrate the rotary table 1710 for drilling the borehole 1712 through the subsurface formations 1714. The drillstring 1708 may include a drill pipe 1718 and a bottom hole assembly (BHA) 1720 (e.g., drill string), perhaps located at the lower portion of the drill pipe 1718.

The BHA 1720 may include a measurement while drilling (MWD) or LWD tool 1760, including the NMR tool 100, and a drill bit 1726. The drill bit 1726 may operate to create the borehole 1712 by penetrating the surface 1704 and the subsurface formations 1714. The NMR tool 100 may be used to determine a condition of pipes that are located in the borehole 1712 as described previously.

During drilling operations within the borehole 1712, the drillstring 1708 (perhaps including the drill pipe 1718 and the BHA 1720) may be rotated by the rotary table 1710 and/or by the mud motor 1790 that is located down hole. The drill collars 1722 may be used to add weight to the drill bit 1726. Drill collars 1722 may also operate to stiffen the BHA 1720, allowing the BHA 1720 to transfer the added weight to the drill bit 1726, and in turn, to assist the drill bit 1726 in penetrating the surface 1704 and subsurface formations 1714.

During drilling operations within the borehole 1712, a mud pump 1732 may pump drilling fluid (sometimes referred to as "drilling mud") from a mud pit 1734 through a hose 1736 into the drill pipe 1718 and down to the drill bit 1726. The drilling fluid can flow out from the drill bit 1726 and be returned to the surface 1704 through an annular area 1740 between the drill pipe 1718 and the sides of the borehole 1712. The drilling fluid may then be returned to the mud pit 1734, where such fluid is filtered. In some examples, the drilling fluid can be used to cool the drill bit 1726, as well as to provide lubrication for the drill bit 1726 during drilling operations. Additionally, the drilling fluid may be used to remove subsurface formation cuttings created by operating the drill bit 1726.

A workstation 1792 including a controller 1796 may include modules comprising hardware circuitry, a processor, and/or memory circuits that may store software program modules and objects, and/or firmware, and combinations thereof that are configured to execute the above-described methods of FIGS. 16 and 17 as instructions.

In an example, the NMR tool 100 may be used to transmit an electromagnetic field and then measure the resulting secondary electromagnetic field responses generated by the pipes being inspected. The resulting data may be transmitted to the surface workstation 1792 via telemetry. The workstation 1792, with its controller 1796, may process that telemetry, execute any methods disclosed herein, and generate a two-dimensional image of the downhole pipes.

Figure 18:
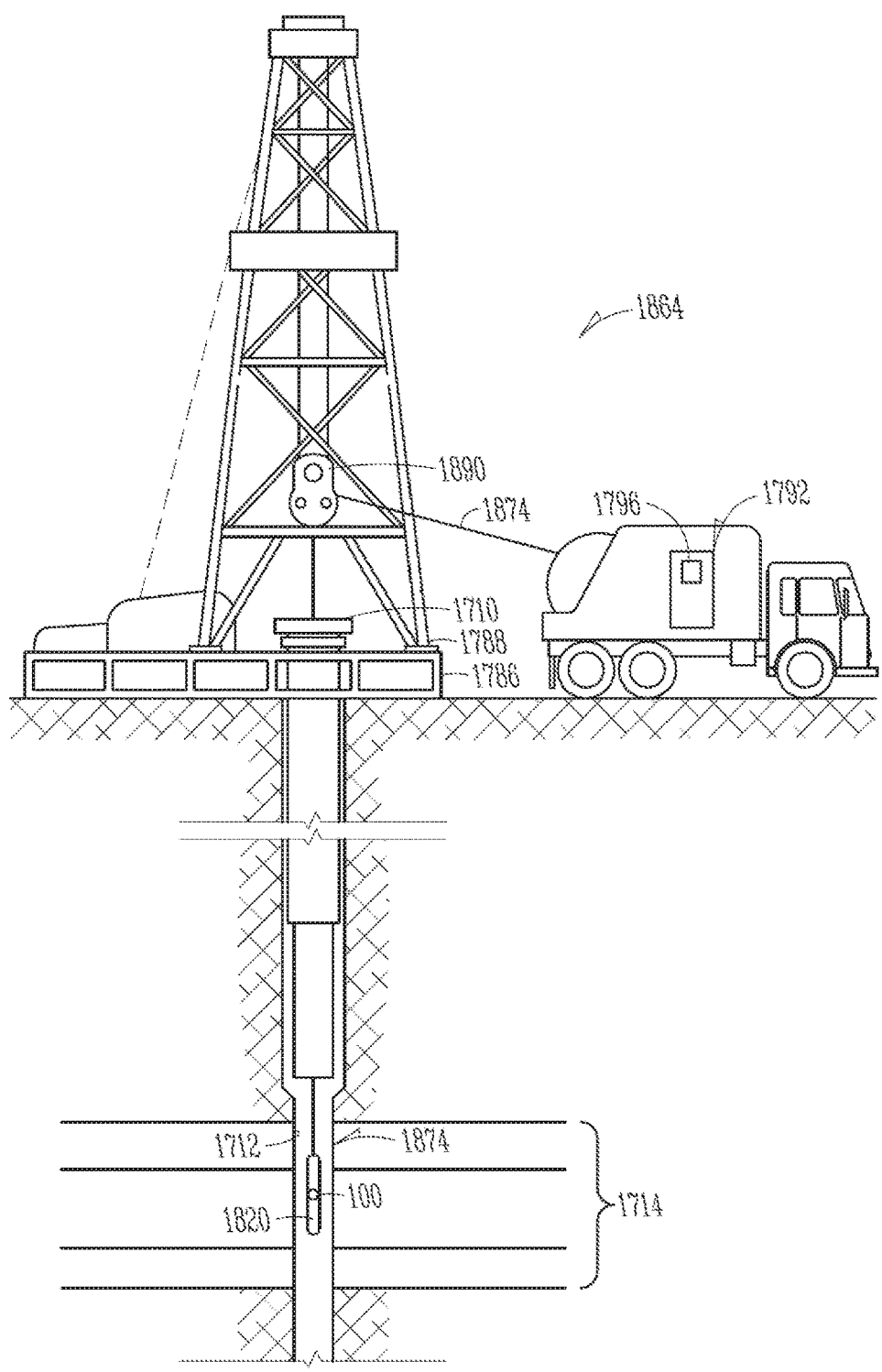
FIG. 18 is a diagram showing a wireline system, according to various examples of the disclosure.

FIG. 18 is a diagram showing a wireline system 1864, according to various examples of the disclosure. The system 1864 may comprise at least one wireline logging tool body 1820, as part of a wireline logging operation in a borehole 1712, including the NMR tool 100 as described previously.

A drilling platform 1786 equipped with a derrick 1788 that supports a hoist 1890 can be seen. Drilling oil and gas wells is commonly carried out using a string of drill pipes connected together so as to form a drillstring that is lowered through a rotary table 1710 into the borehole 1712. Here it is assumed that the drillstring has been temporarily removed from the borehole 1712 to allow the wireline logging tool body 1820, such as a probe or sonde with the inspection tool 100, to be lowered by wireline or logging cable 1874 (e.g., slickline cable) into the borehole 1712. Typically, the wireline logging tool body 1820 is lowered to the bottom of the region of interest and subsequently pulled upward at a substantially constant speed.

During the upward trip, at a series of depths, the NMR tool 100 may be used to determine the characteristics of the formation 1714 or a reservoir in the formation 1714. The resulting data may be communicated to a surface logging facility (e.g., workstation 1792) for processing, analysis, and/or storage. The workstation 1792 may have a controller 1796 that is able to execute any methods disclosed herein.

FIG. 19 is a block diagram of an example system 1900 (e.g., computer system) operable to implement the activities of multiple methods, according to various examples of the disclosure. The system 1900 may include a tool housing 1906 having the NMR tool 100 disposed therein. The system 1900 may be implemented as shown in FIGS. 17 and 18 with reference to the workstation 1792 and controller 1796.

The system 1900 may include circuitry such as a controller 1920, a memory 1930, and a communications device 1935. The memory 1930 may be structured to include a database. The controller 1920, the memory 1930, and the communications device 1935 may be arranged to operate as control circuitry to control operation of the NMR tool 100 and execute any methods disclosed herein in order to determine the characteristics of a fluid and/or formation.

The communications device 1935 may include communications capability for communicating from downhole to the surface or from the surface to downhole. Such communications capability can include a telemetry system such as mud pulse telemetry. In another example, the communications device 1935 may use combinations of wired communication technologies and wireless technologies.

The system 1900 may also include a bus 1937 that provides electrical conductivity among the components of the system 1900. The bus 1937 can include an address bus, a data bus, and a control bus, each independently configured or in an integrated format. The bus 1937 may be realized using a number of different communication mediums that allows for the distribution of components of the system 1900. The bus 1937 may include a network. Use of the bus 1937 may be regulated by the controller 1920.

The system 1900 may include display device(s) 1960 as a distributed component on the surface of a wellbore, which may be used with instructions stored in the memory 1930 to implement a user interface to monitor the operation of the tool 1906 or components distributed within the system 1900. The user interface may be used to input parameter values for thresholds such that the system 1900 can operate autonomously substantially without user intervention in a variety of applications. The user interface may also provide for manual override and change of control of the system 1900 to a user. Such a user interface may be operated in conjunction with the communications device 1935 and the bus 1937.

These implementations can include a machine-readable storage device having machine-executable instructions, such as a non-transitory computer-readable medium having computer-executable instructions. Further, a computer-readable storage device may be a physical device that stores data represented by a physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Example 1 is a method for shaping a nuclear magnetic resonance (NMR) pulse, the method comprising: adjusting at least one of an amplitude modulation or a phase modulation of a non-adiabatic pulse to produce a modified non-adiabatic pulse; transmitting the modified non-adiabatic pulse into an object; and determining when the non-adiabatic pulse is configured to produce a substantially uniform saturation or inversion of magnetization from the object based on an echo response from the object responsive to the modified non-adiabatic pulse.

In Example 2, the subject matter of Example 1 optionally includes adjusting phase cycling of the non-adiabatic pulse to produce the modified non-adiabatic pulse.

In Example 3, the subject matter of Example 2 optionally includes wherein phase cycling of the non-adiabatic pulse comprises changing the phase of the non-adiabatic pulse through each of a cycle of different values for respective successive measurements.

In Example 4, the subject matter of any one or more of Examples 1-3 optionally include transmitting a readout pulse sequence a wait time after transmitting the modified non-adiabatic pulse into the object.

In Example 5, the subject matter of any one or more of Examples 1-4 optionally include wherein generating the modified non-adiabatic pulse comprises generating a sinc pulse.

In Example 6, the subject matter of any one or more of Examples 1-5 optionally include wherein determining when the non-adiabatic pulse is configured to produce a substantially uniform saturation or inversion response comprises determining the uniform saturation or inversion response based on a field gradient at a bandwidth.

In Example 7, the subject matter of any one or more of Examples 1-6 optionally include wherein determining when the non-adiabatic pulse is configured to produce a substantially uniform saturation or inversion response comprises determining a calculated response from Bloch's equations based on the echo response responsive to transmitting the modified non-adiabatic pulse into the object.

In Example 8, the subject matter of Example 7 optionally includes transmitting the modified non-adiabatic pulse into a fluid in a geological formation; waiting a time period after transmitting; transmitting, after the time period, a readout pulse sequence based on the non-adiabatic pulse; receiving the echo response from the fluid; determining from Bloch's equations if the echo response indicates nuclear spins have recovered to equilibrium; incrementing the time period and repeating the transmitting the readout pulse sequence and receiving the echo response until Bloch's equations indicate that the nuclear spins have recovered to equilibrium at a final wait time; and determining characteristics of the fluid based on the final wait time.

In Example 9, the subject matter of Example 8 optionally includes the final wait time is substantially equal to a $T_1$ relaxation time.

Example 10 is a nuclear magnetic resonance (NMR) device, comprising an NMR device to transmit and receive NMR signals; and control circuitry coupled to the NMR device to generate one or more non-adiabatic saturation pulses based on adjusted amplitude modulation or phase cycling wherein the one or more generated non-adiabatic saturation pulses produce a substantially uniform nuclear spin saturation or nuclear spin inversion response from a fluid.

In Example 11, the subject matter of Example 10 optionally includes wherein the generated pulse produces the substantially uniform nuclear spin saturation or nuclear spin inversion response at a least amount of total radio frequency (RF) energy as determined by Bloch's equations.

In Example 12, the subject matter of any one or more of Examples 10-11 optionally include a downhole tool housing including the NMR device.

In Example 13, the subject matter of Example 12 optionally includes wherein the downhole tool is a wireline tool.

In Example 14, the subject matter of any one or more of Examples 12-13 optionally include wherein the downhole tool is a drill string tool.

Example 15 is a non-transitory computer-readable medium comprising instructions for executing downhole measurements that, when executed by a computer, cause the computer to: adjust at least one of an amplitude modulation or a phase modulation of a non-adiabatic pulse to produce a modified non-adiabatic pulse; generate the modified non-adiabatic pulse to transmit the modified non-adiabatic pulse into a geological formation reservoir; and determine when the non-adiabatic pulse is configured to produce a substantially uniform saturation or inversion of magnetization echo response from the geological formation reservoir.

In Example 16, the subject matter of Example 15 optionally includes wherein the instructions further cause the computer to wait a time prior to controlling transmission of a recovery pulse sequence and receiving the echo response indicative of a percentage of nuclear spin saturation or nuclear spin inversion of the reservoir.

In Example 17, the subject matter of any one or more of Examples 15-16 optionally include transmitting a π/2 pulse into the reservoir after the wait time and prior to transmission of the recovery pulse sequence.

In Example 18, the subject matter of any one or more of Examples 15-17 optionally include wherein the instructions further cause the computer to transmit a pulse into the reservoir, after the wait time and prior to transmission of the recovery pulse sequence, to transition nuclear spins of reservoir fluid from an $M_z$ plane to an $M_x$ and $M_y$ plane.

In Example 19, the subject matter of any one or more of Examples 15-18 optionally include wherein the instructions further cause the computer to: select a non-adiabatic pulse and readout sequence from a plurality of non-adiabatic pulses and read out sequences; determine results for Bloch's equations for the selected non-adiabatic pulse and readout sequence; determine a first proportionality between a peak amplitude of the selected readout sequence and a peak amplitude of the selected non-adiabatic pulse; generate activations for T1 and T2 measurements based on the results of the Bloch's equations; determine an RF amplitude for a readout pulse of the readout sequence; and multiply the first proportionality by a second proportionality determined theoretically to generate a resultant RF amplitude for the non-adiabatic pulse.

In Example 20, the subject matter of any one or more of Examples 15-19 optionally include wherein the instructions further cause the computer to select from the plurality of non-adiabatic pulses and read out sequences comprising AM pulses, FM pulses, or PM pulses.

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of ordinary skill in the art upon studying the above description.

What is claimed is:

1. A method for shaping a nuclear magnetic resonance (NMR) pulse, the method comprising:
   adjusting at least one of an amplitude modulation or a phase modulation of a non-adiabatic pulse to produce a modified non-adiabatic pulse;
   transmitting the modified non-adiabatic pulse into an object;
   determining when the non-adiabatic pulse is configured to produce a substantially uniform saturation or inversion of magnetization from the object based on an echo response from the object responsive to the modified non-adiabatic pulse, wherein determining when the non-adiabatic pulse is configured to produce a substantially uniform saturation or inversion response comprises determining a calculated response from Bloch's equations based on the echo response responsive to transmitting the modified non-adiabatic pulse into the object;

transmitting, after a time period, a readout pulse sequence based on the non-adiabatic pulse;
receiving the echo response from the fluid;
determining from Bloch's equations if the echo response indicates nuclear spins have recovered to equilibrium;
incrementing the time period and repeating the transmitting of the readout pulse sequence and receiving the echo response until Bloch's equations indicate that the nuclear spins have recovered to equilibrium at a final wait time; and
determining characteristics of the fluid based on the final wait time.

2. The method of claim 1, further comprising adjusting phase cycling of the non-adiabatic pulse to produce the modified non-adiabatic pulse.

3. The method of claim 2, wherein phase cycling of the non-adiabatic pulse comprises changing the phase of the non-adiabatic pulse through each of a cycle of different values for respective successive measurements.

4. The method of claim 1, further comprising transmitting a readout pulse sequence a wait time after transmitting the modified non-adiabatic pulse into the object.

5. The method of claim 1, wherein generating the modified non-adiabatic pulse comprises generating a sinc pulse.

6. The method of claim 1, wherein determining when the non-adiabatic pulse is configured to produce a substantially uniform saturation or inversion response comprises determining the uniform saturation or inversion response based on a field gradient at a bandwidth.

7. The method of claim 1, wherein the final wait time is substantially equal to a $T_1$ relaxation time.

8. A nuclear magnetic resonance (NMR) device, comprising
an NMR device to transmit and receive NMR signals; and
control circuitry coupled to the NMR device where the control circuitry is configured to:
generate one or more non-adiabatic saturation pulses based on adjusted amplitude modulation or phase cycling wherein the one or more generated non-adiabatic saturation pulses produce a substantially uniform nuclear spin saturation or nuclear spin inversion response from a fluid;
adjust at least one of an amplitude modulation or a phase modulation of a non-adiabatic pulse to produce a modified non-adiabatic pulse;
transmit the modified non-adiabatic pulse into an object;
determine when the non-adiabatic pulse is configured to produce a substantially uniform saturation or inversion of magnetization from the object based on an echo response from the object responsive to the modified non-adiabatic pulse;
determine when the non-adiabatic pulse is configured to produce a substantially uniform saturation or inversion response by determining a calculated response from Bloch's equations based on the echo response responsive to transmitting the modified non-adiabatic pulse into the object;
transmit, after a time period, a readout pulse sequence based on the non-adiabatic pulse;
receive the echo response from the fluid;
determine from Bloch's equations if the echo response indicates nuclear spins have recovered to equilibrium;
increment the time period and repeat the transmitting of the readout pulse sequence and receiving the echo response until Bloch's equations indicate that the nuclear spins have recovered to equilibrium at a final wait time; and
determine characteristics of the fluid based on the final wait time.

9. The NMR device of claim 8, wherein the generated pulse produces the substantially uniform nuclear spin saturation or nuclear spin inversion response at a least amount of total radio frequency (RF) energy as determined by Bloch's equations.

10. The NMR device of claim 8, further comprising a downhole tool housing including the NMR device.

11. The NMR device of claim 10, wherein the downhole tool is a wireline tool.

12. The NMR device of claim 10, wherein the downhole tool is a drill string tool.

13. A non-transitory computer-readable medium comprising instructions for executing downhole measurements that, when executed by a computer, cause the computer to:
adjust at least one of an amplitude modulation or a phase modulation of a non-adiabatic pulse to produce a modified non-adiabatic pulse;
generate the modified non-adiabatic pulse to transmit the modified non-adiabatic pulse into a geological formation reservoir;
determine when the non-adiabatic pulse is configured to produce a substantially uniform saturation or inversion of magnetization echo response from the geological formation reservoir;
select a non-adiabatic pulse and readout sequence from a plurality of non-adiabatic pulses and read out sequences;
determine results for Bloch's equations for the selected non-adiabatic pulse and readout sequence;
determine a first proportionality between a peak amplitude of the selected readout sequence and a peak amplitude of the selected non-adiabatic pulse;
generate activations for $T_1$ and $T_2$ measurements based on the results of the Bloch's equations;
determine an RF amplitude for a readout pulse of the readout sequence; and
multiply the first proportionality by a second proportionality determined theoretically to generate a resultant RF amplitude for the non-adiabatic pulse.

14. The non-transitory computer-readable medium of claim 13, wherein the instructions further cause the computer to wait a time prior to controlling transmission of a recovery pulse sequence and receiving the echo response indicative of a percentage of nuclear spin saturation or nuclear spin inversion of the reservoir.

15. The non-transitory computer-readable medium of claim 13, wherein the instructions further cause the computer to transmit a $\pi/2$ pulse into the reservoir after the wait time and prior to transmission of the recovery pulse sequence.

16. The non-transitory computer-readable medium of claim 13, wherein the instructions further cause the computer to transmit a pulse into the reservoir, after the wait time and prior to transmission of the recovery pulse sequence, to transition nuclear spins of reservoir fluid from an $M_z$ plane to an $M_x$ and $M_y$ plane.

17. The non-transitory computer-readable medium of claim 13, wherein the instructions further cause the computer to select from the plurality of non-adiabatic pulses and read out sequences comprising AM pulses, FM pulses, or PM pulses.

* * * * *